United States Patent
Jang et al.

(10) Patent No.: US 10,360,806 B2
(45) Date of Patent: Jul. 23, 2019

(54) METHOD AND APPARATUS FOR PROVIDING EXERCISE PROGRAM BASED ON FEEDBACK

(71) Applicants: Samsung Electronics Co., Ltd., Suwon-si (KR); University-Industry Cooperation Group of Kyung Hee University, Yongin-si (KR)

(72) Inventors: Dae-Geun Jang, Yongin-si (KR); Choonghee Lee, Seoul (KR); Byunghoon Ko, Hwaseong-si (KR); SangKon Bae, Seongnam-si (KR); Youn-ho Kim, Hwaseong-si (KR); Sub Sunoo, Yongin-si (KR); Sang Seok Nam, Suwon-si (KR); Hun Young Park, Incheon (KR)

(73) Assignee: Samsung Electronics Co., Ltd., Suwon-si (KR)

(*) Notice: Subject to any disclaimer, the term of this patent is extended or adjusted under 35 U.S.C. 154(b) by 435 days.

(21) Appl. No.: 15/059,879

(22) Filed: Mar. 3, 2016

(65) Prior Publication Data
US 2016/0354636 A1 Dec. 8, 2016

(30) Foreign Application Priority Data
Jun. 4, 2015 (KR) .................. 10-2015-0078991

(51) Int. Cl.
*G09B 5/00* (2006.01)
*A61B 5/024* (2006.01)
(Continued)

(52) U.S. Cl.
CPC ............ *G09B 5/00* (2013.01); *A61B 5/02438* (2013.01); *A61B 5/1118* (2013.01); *A61B 5/681* (2013.01);
(Continued)

(58) Field of Classification Search
CPC .............. A63B 5/04; A63B 24/00; A63B 5/02
See application file for complete search history.

(56) References Cited

U.S. PATENT DOCUMENTS 5,318,487 A * 6/1994 Golen .................... A61B 5/222
482/3
5,769,755 A * 6/1998 Henry ................ A63B 71/0622
116/212
(Continued)

FOREIGN PATENT DOCUMENTS

JP 2002-153430 A 5/2002
JP 2003-24287 A 1/2003
(Continued)

OTHER PUBLICATIONS

"EPOC Based Training Effect Assessment." *White paper by Firstbeat Technologies Ltd.* (Sep. 2005): pp. 1-5. (in English).
(Continued)

*Primary Examiner* — Jason Skaarup
(74) *Attorney, Agent, or Firm* — NSIP Law

(57) ABSTRACT

A method of providing an exercise program includes providing a coaching message to coach a training pace in an exercise program based on a heart rate of a user performing the exercise program, adjusting an exercise intensity of a current set of exercises of the exercise program based on the coaching message, and providing the exercise program based on the adjusted exercise intensity.

21 Claims, 13 Drawing Sheets

(51) Int. Cl.
- *A61B 5/00* (2006.01)
- *A61B 5/11* (2006.01)
- *G06F 19/00* (2018.01)
- *G09B 7/02* (2006.01)
- *G09B 7/04* (2006.01)
- *G09B 19/00* (2006.01)
- *G09B 23/28* (2006.01)
- *H04W 4/80* (2018.01)

(52) U.S. Cl.
CPC .......... *A61B 5/742* (2013.01); *G06F 19/3481* (2013.01); *G09B 7/02* (2013.01); *G09B 7/04* (2013.01); *G09B 19/0038* (2013.01); *G09B 23/28* (2013.01); *H04W 4/80* (2018.02); *A61B 2503/10* (2013.01)

(56) References Cited

U.S. PATENT DOCUMENTS

| | | | |
|---|---|---|---|
| 7,717,827 B2 | 5/2010 | Kurunmaki et al. | |
| 8,052,580 B2 | 11/2011 | Saalasti et al. | |
| 8,200,323 B2* | 6/2012 | DiBenedetto | A63B 24/0062 482/8 |
| 8,465,397 B2 | 6/2013 | Saalasti et al. | |
| 9,615,785 B2* | 4/2017 | Rocker | A61B 5/024 |
| 2004/0077462 A1* | 4/2004 | Brown | A63B 24/0084 482/8 |
| 2005/0124463 A1* | 6/2005 | Yeo | A61B 5/02427 482/8 |
| 2005/0288154 A1* | 12/2005 | Lee | A63B 24/0084 482/3 |
| 2006/0004265 A1* | 1/2006 | Pulkkinen | A61B 5/0205 600/300 |
| 2006/0097879 A1* | 5/2006 | Lippincott | A61B 5/02055 340/573.1 |
| 2008/0153671 A1* | 6/2008 | Ogg | A63B 71/0686 482/3 |
| 2008/0280730 A1* | 11/2008 | Alexanderson | A63B 24/0062 482/9 |
| 2009/0069156 A1* | 3/2009 | Kurunmaki | A63B 24/0062 482/9 |
| 2009/0312658 A1* | 12/2009 | Thieberger | A63B 24/0062 600/520 |
| 2010/0088023 A1* | 4/2010 | Werner | A63B 24/0021 701/467 |
| 2010/0216601 A1* | 8/2010 | Saalasti | A61B 5/024 482/8 |
| 2011/0152696 A1* | 6/2011 | Ryan | A61B 5/222 600/481 |
| 2012/0015779 A1* | 1/2012 | Powch | A61B 5/02055 482/9 |
| 2014/0288448 A1 | 9/2014 | Saalasti et al. | |
| 2017/0143262 A1* | 5/2017 | Kurunmaki | A61B 5/0255 |

FOREIGN PATENT DOCUMENTS

| | | |
|---|---|---|
| JP | 2006-255028 A | 9/2006 |
| JP | 2009-142333 A | 7/2009 |
| KR | 10-0533105 B1 | 12/2005 |
| KR | 10-2010-0103972 A | 9/2010 |
| KR | 10-2011-0044113 A | 4/2011 |
| KR | 10-1140740 B1 | 5/2012 |
| KR | 10-2016-0047153 A | 5/2016 |
| KR | 10-2016-0048567 A | 5/2016 |
| KR | 10-2016-0091694 A | 8/2016 |

OTHER PUBLICATIONS

"Indirect E. P. O. C. Prediction Method Based on Heart Rate Measurement." *White paper by Firstbeat Technologies Ltd* (May 2005): pp. 1-5. (in English).

"Automated Fitness Level (VO2max) Estimation with Heart Rate and Speed Data." *White paper by Firstbeat Technologies Ltd.* (Jul. 2014): pp. 1-9. (in English).

* cited by examiner

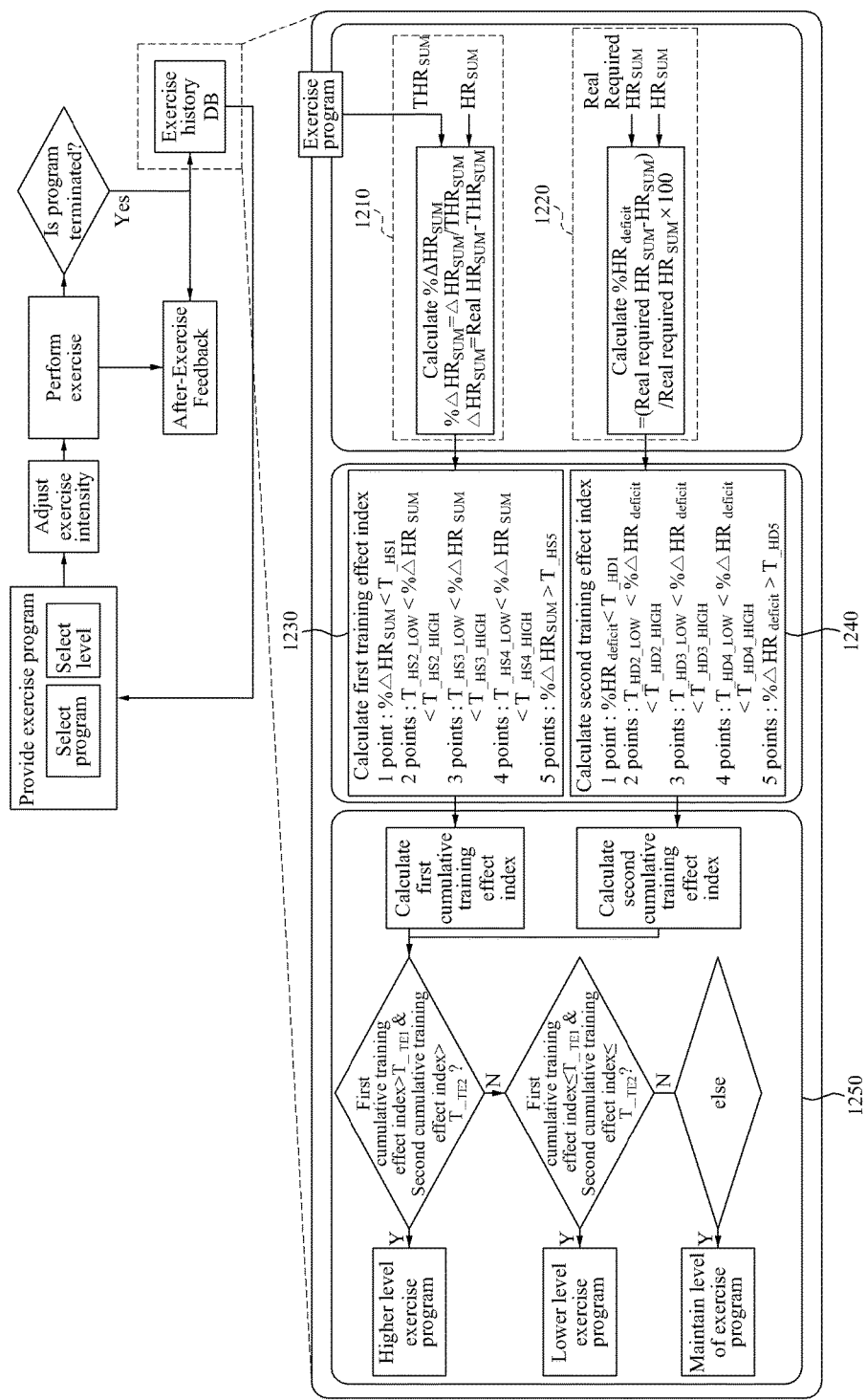

METHOD AND APPARATUS FOR PROVIDING EXERCISE PROGRAM BASED ON FEEDBACK

CROSS-REFERENCE TO RELATED APPLICATION(S)

This application claims the benefit under 35 USC 119(a) of Korean Patent Application No. 10-2015-0078991 filed on Jun. 4, 2015, in the Korean Intellectual Property Office, the entire disclosure of which is incorporated herein by reference for all purposes.

BACKGROUND

1. Field

The following description relates to a method and an apparatus for providing an exercise program based on a feedback.

2. Description of Related Art

In general, an exercise program suggests an appropriate exercise intensity to a user based on a ventilatory threshold, a lactate threshold, or oxygen consumption estimated based on personal body information and heart rate information measured through a sensor attached to a body of the user. The ventilatory threshold, the lactate threshold, and the oxygen consumption may be estimated based on a linear relationship between heart rate information and a metabolic demand. However, the heart rate information may have a non-linear relationship with the metabolic demand according to an increase in an exercise intensity. Thus, accuracy may be limited when an individual exercise intensity is determined based on heart rate information. Further, users have different heart rates and different heartbeat patterns. Thus, in a case of using only the generalized values, an inaccurate exercise intensity may be suggested to a user. In a worst case scenario, the user go into shock due to an excessive level of exercise.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a method of providing an exercise program includes providing a coaching message to coach a training pace in an exercise program based on a heart rate of a user performing the exercise program; adjusting an exercise intensity of a current set of exercises of the exercise program based on the coaching message; and providing the exercise program based on the adjusted exercise intensity.

The coaching message may be any one or any combination of any two or more of a first coaching message for reducing the training pace, a second coaching message for maintaining the training pace, and a third coaching message for increasing the training pace.

The providing may include providing one of the first coaching message, the second coaching message, and the third coaching message based on a variation in the heart rate and a difference between the heart rate and a preset target heart rate.

The adjusting may include counting a number of times that each of the first coaching message and the third coaching message is consecutively provided; and adjusting the exercise intensity of the current set of exercises in response to a result of the counting being greater than a preset number of times.

The method may further include adjusting an exercise level of the exercise program after a termination of the exercise program based on any one or any combination of any two or more of a heart rate of the user measured during an exercise of the current set, a rating of perceived exertion (RPE) of the user for the exercise of the current set, and a coaching message history of the current set.

The adjusting may include any one or any combination of any two or more of calculating a cumulative heart rate difference rate based on a preset target cumulative heart rate and a first cumulative heart rate, the preset target cumulative heart rate being based on a preset target heart rate of the user during the exercise of the current set of exercises, and the first cumulative heart rate being based on the heart rate of the user measured during the exercise of the current set of exercises; calculating a message score based on the coaching message history; and calculating a time score based on a time during which the measured heart rate is higher than a preset target heart rate and a time during which the measured heart rate is lower than the preset target heart rate.

The calculating of the message score may include calculating the message score by applying a first weight to a number of times the first coaching message was provided in the coaching message history, a second weight to a number of times the second coaching message was provided in the coaching message history, and a third weight to a number of times the third coaching message was provided in the coaching message history.

The adjusting may include adjusting the exercise level of the exercise program based on any one or any combination of any two or more of the cumulative heart rate difference rate, the message score, and the time score.

The adjusting may include changing the exercise program based on the RPE of the user, and any one or any combination of any two or more of the cumulative heart rate difference rate, the message score, and the time score.

The method may further include storing, in an exercise history database, exercise history information including any one or any combination of any two or more of a training result of the current set, a heart rate measured during the exercise of the current set, the RPE of the user for the exercise of the current set, and a coaching history based on the coaching message history of the current set.

The exercise program may include a plurality of sets of exercises including the current set of exercises; and the method further may include obtaining a training effect index for each set of exercises based on exercise history information of the exercise program; obtaining a cumulative training effect index for each set of exercises; and changing the exercise program based on the cumulative training effect index.

The obtaining of the training effect index may include obtaining a first training effect index based on a preset target cumulative heart rate and a first cumulative heart rate, the preset target cumulative heart rate being based on a preset target heart rate of the user during an exercise of the current set of exercises, and the first cumulative heart rate being based on a heart rate of the user measured during the exercise of the current set of exercises; and obtaining a second training effect index based on an anaerobic energy consumption rate based on the first cumulative heart rate and a second cumulative heart rate, the second cumulative heart rate being based on a steady-state heart rate of the user measured during the exercise.

The obtaining of the first training effect index may include calculating a cumulative heart rate difference rate based on the first cumulative heart rate and the preset target cumulative heart rate; and obtaining the first training effect index based on a result of comparing the cumulative heart rate difference rate to a preset threshold.

The obtaining of the second training effect index may include calculating the anaerobic energy consumption rate based on the first cumulative heart rate and the second cumulative heart rate; and obtaining the second training effect index based on a result of comparing the anaerobic energy consumption rate to a preset threshold.

The changing may include comparing the cumulative training effect index to a preset threshold; and changing the exercise program based on a result of the comparing.

In another general aspect, a non-transitory computer-readable storage medium stores instructions to control a processor to perform the method described above.

In another general aspect, an apparatus for providing an exercise program includes a measurer configured to measure a heart rate of a user performing an exercise program; and a processor configured to provide a coaching message for coaching a training pace in the exercise program based on the heart rate, adjust an exercise intensity of a current set of exercises of the exercise program based on the coaching message, and provide the exercise program based on the adjusted exercise intensity.

The processor may be further configured to provide any one or any combination of any two or more of a first coaching message, a second coaching message, and a third coaching message based on a variation in the heart rate and a difference between the heart rate and a preset target heart rate, and adjust the exercise intensity of the current set of exercises in response to a number of times that each of the first coaching message and the third coaching message is consecutively provided being greater than a preset number of times.

The processor may be further configured to calculate, after a termination of the exercise program, any one or any combination of any two or more of a cumulative heart rate difference rate based on a preset target cumulative heart rate and a first cumulative heart rate, the preset target cumulative heart rate being based on a preset target heart rate of the user during an exercise of the current set of exercises, and the first cumulative heart rate being based on a heart rate of the user measured during the exercise of the current set; a message score based on a coaching message history; and a time score based on a time during which the heart rate measured during the exercise of the current set is higher than a preset target heart rate and a time during which the measured heart rate is lower than the preset target heart rate; and the processor may be further configured to adjust an exercise level of the exercise program based on any one or any combination of any two or more of the cumulative heart rate difference rate, the message score, and the time score.

The exercise program may include a plurality of sets of exercises including the current set of exercises; and the processor may be further configured to obtain a training effect index for each set of exercises based on exercise history information of the exercise program, obtain a cumulative training effect index for each set of exercises, and change the exercise program based on the cumulative training effect index.

Other features and aspects will be apparent from the following detailed description, the drawings, and the claims.

BRIEF DESCRIPTION OF THE DRAWINGS

FIG. 12 illustrates an example of a method of changing an exercise program using a feedback based on a training history of the exercise program.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

The terminology used herein is for the purpose of describing particular examples only, and is not to limit the disclosure. As used herein, the singular forms "a", "an", and "the" are intended to include the plural forms as well, unless the context clearly indicates otherwise. As used herein, the terms "include," "comprise," and "have" specify the presence of stated features, numbers, operations, elements, components, and combinations thereof, but do not preclude the presence or addition of one or more other features, numbers, operations, elements, components, and combinations thereof.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not be interpreted in an idealized or overly formal sense unless expressly so defined herein.

Figure 1A:
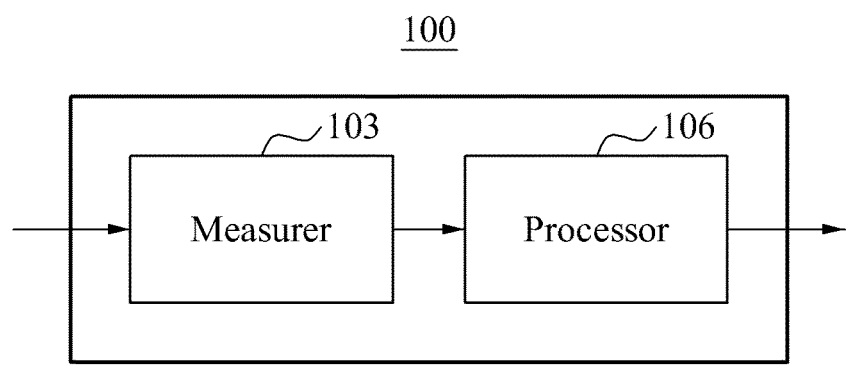
FIGS. 1A and 1B illustrate an example of an apparatus for providing an exercise program and examples of devices in which the apparatus is embedded.
Figure 1B:
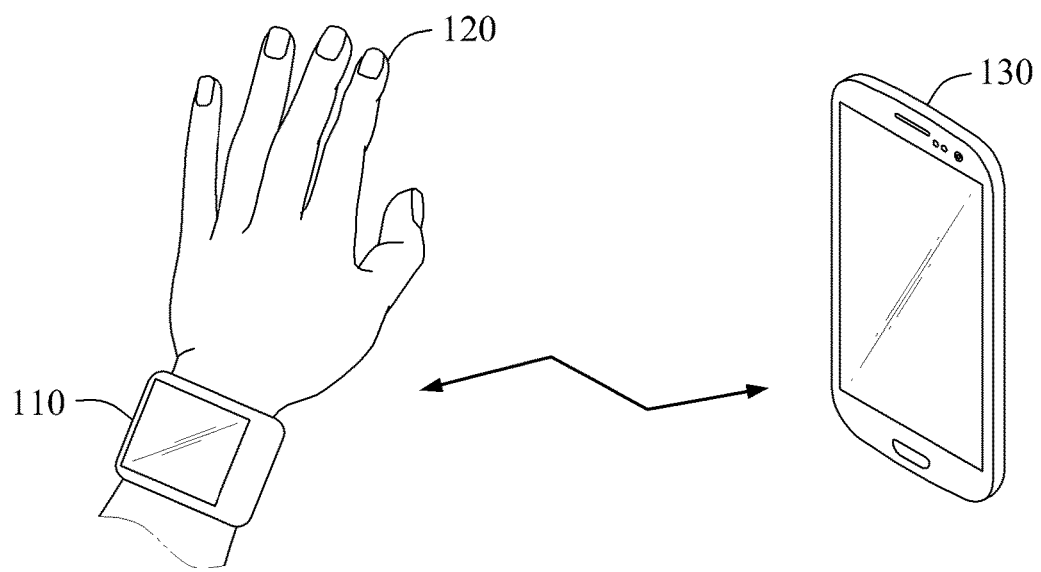

FIGS. 1A and 1B illustrate an example of an apparatus 100 for providing an exercise program and examples of devices in which the apparatus 100 is embedded.

FIG. 1A illustrates an example of an apparatus 100 for providing an exercise program. FIG. 1B illustrates examples of devices in which the apparatus 100 is embedded.

Referring to FIG. 1A, the apparatus 100 includes a measurer 103 and a processor 106.

The measurer 103 measures a heart rate of a user performing an exercise program. The measurer 103 measures the heart rate of the user continuously or at a predetermined time interval while the exercise program is being performed.

The processor 106 provides a coaching message to the user based on the heart rate measured by the measurer 103. The coaching message may be, for example, a message for coaching or guiding the training pace of the exercise program. Examples of the coaching message include a first coaching message for reducing the training pace, a second coaching message for maintaining the training pace, and a third coaching message for increasing the training pace. Additionally, the coaching message may be an alert message for suspending performance of the exercise program.

The processor 106 provides any one or any combination of any two or more of the first coaching message, the second coaching message, and the third coaching message based on $\Delta HR$ denoting a variation in the heart rate, and a difference between the heart rate and a preset target heart rate. The difference may be obtained by calculating $HR-THR$, where HR denotes the heart rate and THR denotes the preset target heart rate. The variation in the heart rate $\Delta HR$ is a degree of a change in the heart rate based on a unit for a predetermined period of time. When a user suffers from a cardiovascular disease, and when a variation in a heart rate of the user exceeds a predetermined level, the processor 106 may provide an alert message to protect the user from a cardiovascular risk. Parameters related to the heart rate will be described with reference to FIG. 4.

The processor 106 adjusts an exercise intensity of a current set of the exercise program based on the coaching message, and provides the exercise program based on the adjusted exercise intensity. As an example, the processor 106 adjusts the exercise intensity of the current set when a number of times that each of the first coaching message and the third coaching message is consecutively provided exceeds a predetermined number of times for example, three times. A current set of exercises is a set of exercises currently being performed by the user. As an example, the user may have completed first, second, and third sets of exercises, and be currently performing a fourth set of exercises. In this example, the first, second, and third sets of exercises may also be referred to as previous sets of exercises, and the fourth set of exercises may also be referred to as the current set of exercises. Also, a fifth set of exercises to be performed by the user after a termination of the fourth set of exercises may also be referred to as a subsequent set of exercises.

A method of generating the coaching message and a method of adjusting an exercise intensity of the current set of the exercise program based on the coaching message in the processor 106 will be described with reference to FIGS. 7 through 8B.

After a termination of the current set of the exercise program, the processor 106 calculates a cumulative heart rate difference rate $\%\Delta HR_{SUM}$ using a preset target cumulative heart rate $THR_{sum}$ and a first cumulative heart rate $HR_{sum}$ based on the heart rate measured in the current set of exercises. The processor 106 calculates a message MScore based on a history of the coaching messages that have been provided. Also, the processor 106 calculates a time score TScore based on the heart rate measured in the current set of exercises. The time score is calculated based on a time during which the measured heart rate is higher than a preset target heart rate and a time during which the measured heart rate is lower than the preset target heart rate.

The processor 106 adjusts an exercise level of the exercise program based on any one or any combination of any two or more of the cumulative heart rate difference rate, the message score, and the time score. A method of calculating the cumulative heart rate difference rate, the message score, and the time score and a method of adjusting the exercise level based on a result of the adjusting in the processor 106 will be described with reference to FIG. 10.

The processor 106 obtains a training effect index for each set of exercises based on exercise history information of the exercise program. The training effect index includes, for example, a first training effect index indicating a qualitative training effect and a second training effect index indicating a quantitative training effect. The processor 106 changes the exercise program using the training effect index obtained for each set of exercises.

A method of obtaining the training effect index and a method of changing the exercise program based on the obtained training effect index in the processor 106 will be described with reference to FIG. 12.

In one example, the apparatus 100 provides an optimal exercise program for a user through a feedback based on a training history during an exercise and after a termination of the exercise program. A method in which the apparatus 100 provides the exercise program through a feedback based on a training history during an exercise and after a termination of the exercise program will be described with reference to the drawings.

Referring to FIG. 1B, the apparatus 100 is included in a wearable device 110 and a mobile device 130.

The apparatus 100 operating in the wearable device 110 will be described as an example as follows. The wearable device 110 may be provided in a form of, for example, a necklace or a device worn on the wrist, such as a watch, a bracelet, or any other device that is worn on the wrist. When a user 120 wearing the wearable device 110 performs an exercise, the apparatus 100 adjusts an exercise intensity of the exercise program in real time based on a heart rate measured from a wrist of the user 120. The apparatus 100 provides the exercise program to the user 120 based on the adjusted exercise intensity.

The wearable device 110 including the apparatus 100 may operate in conjunction with the mobile device 130 and share data with the mobile device 130. For example, the heart rate measured from the user 120 and the exercise program adjusted by the apparatus 100 may be transmitted to the mobile device 130. Also, the mobile device 130 may transmit, to the apparatus 100, exercise history information including, for example, a training result of a previous set of exercises, a heart rate measured in the previous set of exercises, a rating of perceived exertion (RPE) of a user with respect to the previous set of exercises, and a coaching history based on coaching messages provided in the previous set of exercises.

In one example, the processor 106 of the apparatus 100 may be included in the mobile device 130 and the measurer 103 may be included in the wearable device 110. The wearable device 110 is worn on a body part, for example, a wrist, of the user 120 to measure the heart rate of the user 120 from the wrist. The wearable device 110 amplifies and filters the measured heart rate. The wearable device 110 transmits the measured heart rate to the mobile device 130. The apparatus 100 included in the mobile device 130 adjusts an exercise level and an exercise intensity of the exercise program performed by the user 120 based on the heart rate received from the wearable device 110. The term "exercise level" refers to a predetermined step of the exercise program in progress. When one exercise level of the exercise program ends, a next exercise level of the exercise program may automatically start. The term "exercise intensity" refers to an amount of exercise at an exercise level, for example, a number of repetitions of an exercise or a duration of the exercise. Alternatively, the apparatus 100 may change the exercise program. An example in which the measurer 103 is provided separate from the processor 106 will be described with reference to FIG. 2.

Figure 2:
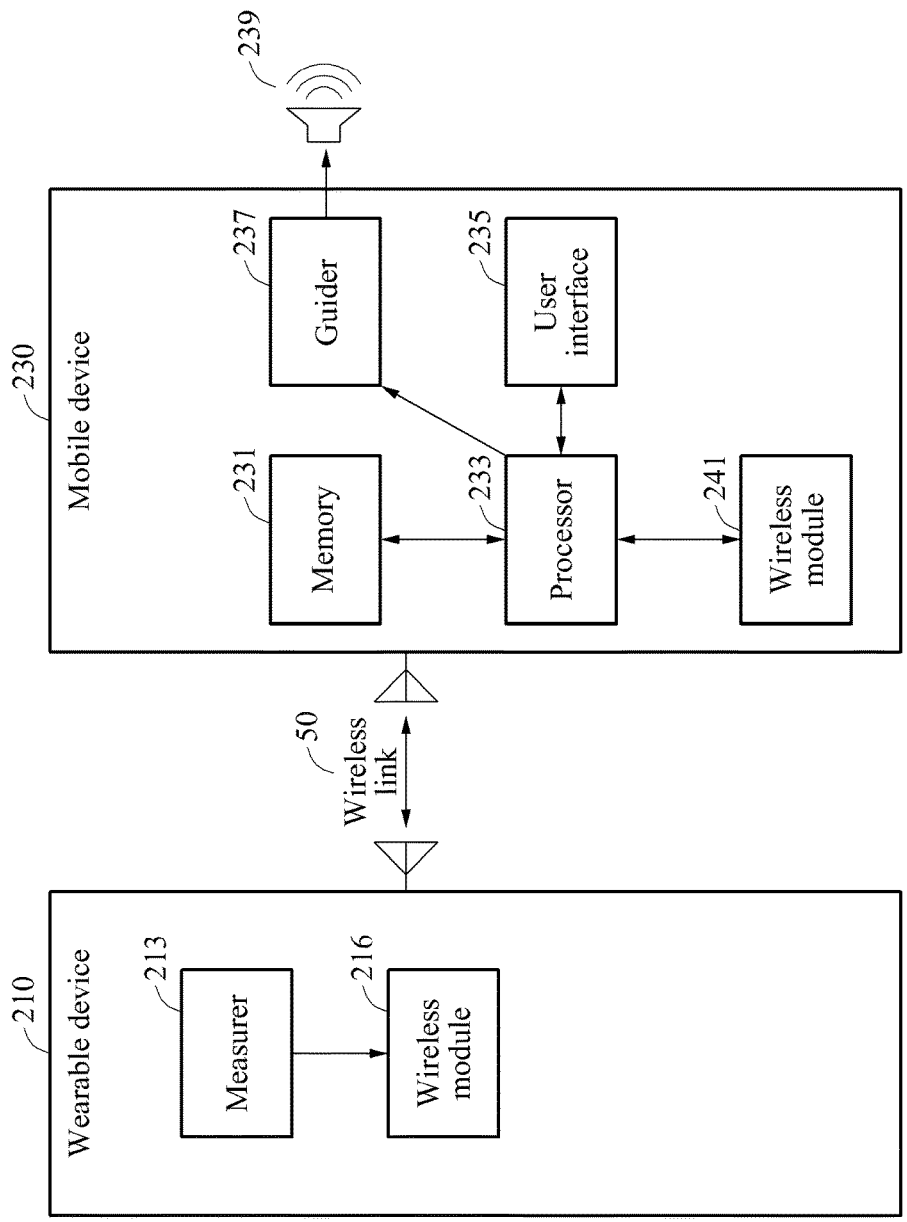
FIG. 2 illustrates an example of an apparatus for providing an exercise program.

FIG. 2 illustrates an example of an apparatus for providing an exercise program. Hereinafter, the apparatus for providing an exercise program may also be referred to as a providing apparatus.

Referring to FIG. 2, a measurer 213 of the providing apparatus is included in a wearable device 210, and a processor 233 of the providing apparatus is included in a mobile device 230.

In this example, the wearable device 210 is connected to the mobile device 230 through a wireless link 50.

The wearable device 210 and the mobile device 230 may include, for example, a wireless Internet interface, such as a wireless local area network (WLAN) interface, a WiFi interface, a digital living network alliance (DLNA) interface, a wireless broadband (WiBro) interface, a world interoperability for microwave access (WiMAX) interface, or a high-speed downlink packet access (HSDPA), and a local communication interface, such as a Bluetooth™ interface, a radio frequency identification (RFID) interface, an infrared data association (IrDA) interface, an ultra wideband interface, a ZigBee interface, or a near field communication (NFC) interface.

The wearable device 210 includes the measurer 213 configured to measure a heart rate. The measurer 213 may be, for example, a photoplethysmogram (PPG) sensor. The measurer 213 measures the heart rate by sensing a potential signal or other parameter of a body part in which the heart rate of a user is measured. The measurer 213 measures the heart rate of the user on, for example, a chest, a fingertip, a wrist, or a forearm of the user. The heart rate is measured using the wearable device 210 while the user performs an exercise, and is then transmitted to the mobile device 230 through a wireless module 216 including the wireless Internet interface and/or the local communication interface.

The wearable device 210 monitors in real time information on a training status of the user whose heart rate is being measured. The information may be transmitted to the mobile device 230 through, for example, the Bluetooth™, the WiFi, the ZigBee, and a customized communication channel using a security function.

The mobile device 230 may be implemented as, for example, a tablet computer, a smartphone, or a personal digital assistant (PDA). Also, the mobile device 230 may be a network device such as a server. The mobile device 230 may be a single server computer or a system similar to the single server computer. Alternatively, the mobile device 230 may be a server cloud distributed in a spatially different positions or one or more server banks.

The mobile device 230 receives various biosignals in addition to the heart rate through the wearable device 210 or another measuring device (not shown). A rating of perceived exertion (RPE) recognized by the user while performing the exercise program or after a termination of the exercise program is input from the user through the wearable device 210 or the mobile device 230.

The mobile device 230 provides a coaching message to coach a training pace based on the heart rate measured by the wearable device 210. Also, the mobile device 230 adjusts an exercise level of the exercise program based on the heart rate and the RPE.

The mobile device 230 includes a memory 231, a processor 233, a user interface 235, a guider 237, and a wireless module 241.

The memory 231 stores an exercise history database including exercise history information related to a previous set of exercises and a current set of exercises. The exercise history database includes the exercise history information including, for example, a training result for each set of exercises, a heart rate measured in each set of exercises, an RPE of the user for each set of exercises, and a coaching history based on a coaching message of each set of exercises.

The processor 233 provides the coaching message to coach the training pace of the exercise program based on the heart rate received from the wearable device 210. The processor 233 adjusts an exercise intensity of the current set of the exercise program based on the coaching message and provides the exercise program based on the adjusted exercise intensity. The description of the processor 106 of FIG. 1 is also applicable to the processor 233 of FIG. 2, and thus will be omitted for increased clarity and conciseness.

The user interface 235 receives the RPE recognized by the user during the performing of the exercise program or after a termination of the exercise program as an input in any of various forms. The RPE may be input to the mobile device 230 through the user interface 235 in a form of, for example, a touch input of the user received through a touch display (not shown), a voice input of the user received through a microphone (not shown), a degree to which the mobile device 230 is tilted or shaken due to the user tilting or shaking the mobile device 230 horizontally or vertically, or a gesture of the user captured by a photographing device.

The user interface 235 displays, for example, a plurality of levels corresponding to exercise intensities on the touch display to receive the RPE of the user. The user inputs the exercise intensity recognized by the user, that is, the RPE, by selecting one of the levels displayed on the touch display. A flexible display may be used as the touch display.

The guider 237 delivers the coaching message from the processor 233 to the user in a form of, for example, an audio guide or a vibration. The coaching message may be the audio guide indicating, for example, "Keep the current pace", "Increase the pace," or "Reduce the pace." The coaching message may also be provided in a form of, for example, one vibration to increase the pace, two vibrations to keep the current pace, and three vibrations to reduce the pace.

The guider 237 may also output an audio guide to a speaker 239. The speaker 239 provides an audio guide output from the guider 237 to receive the RPE of the user. The audio guide may indicate, for example, "How do you feel about a current exercise intensity?", and "Select a level you recognize as the current exercise intensity from levels 1 through 10, with level 10 being the highest level." In response to the audio guide provided through the speaker 237, the user may respond by saying, for example, "too easy", "too hard", or "normal", or "level 1", "level 5," or "level 10." A response of the user corresponds to the RPE of the user, and is delivered to the processor 233 through the user interface 235, the microphone (not shown), or other device.

The wireless module 241 receives heart rate information transmitted from the wireless module 216 of the wearable device 210 through a wireless Internet interface and/or a local communication interface.

Figure 3:
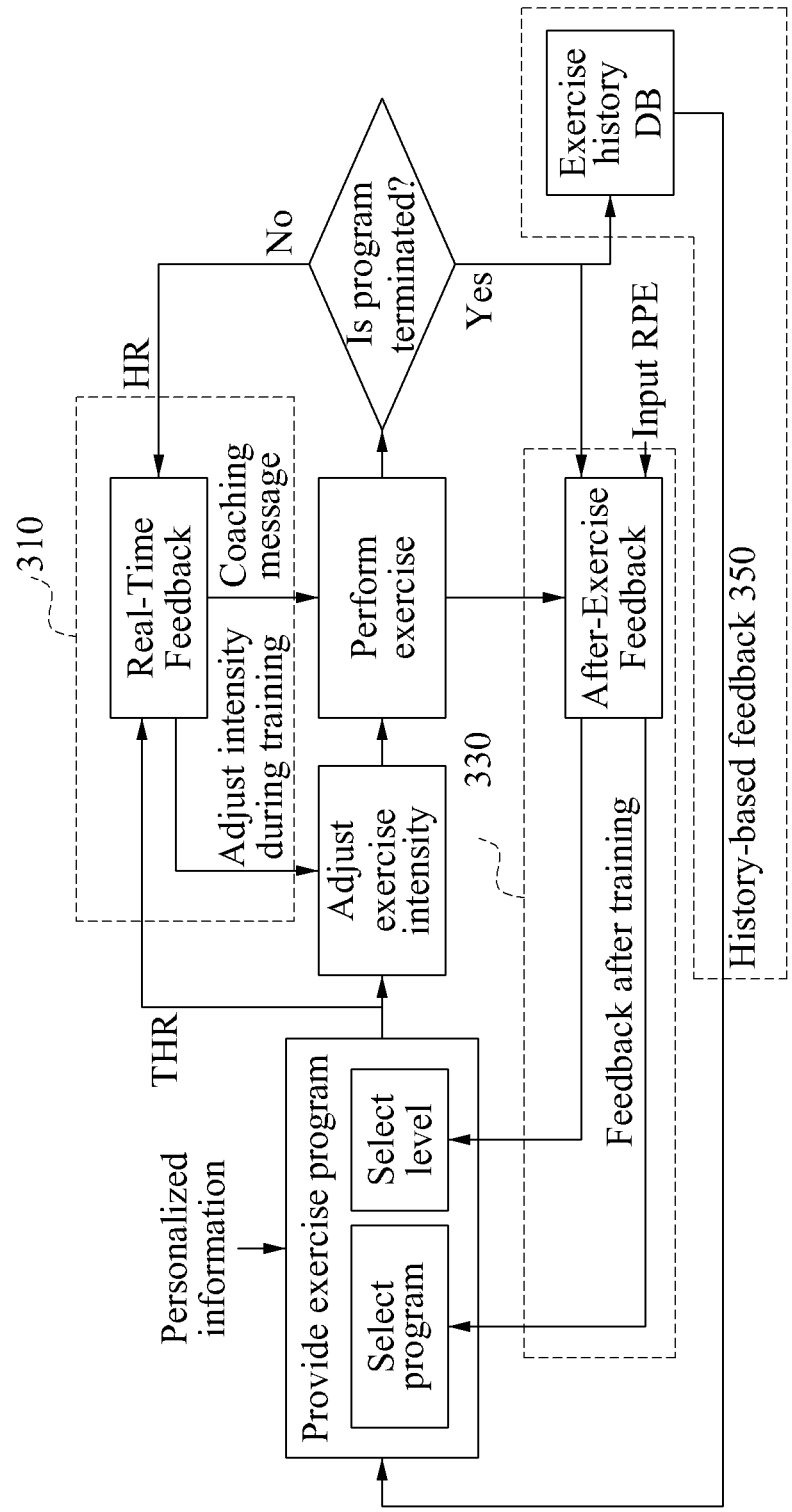
FIG. 3 illustrates an example of a method of providing an exercise program.

FIG. 3 illustrates an example of a method of providing an exercise program.

Referring to FIG. 3, feedbacks 310, 330, and 350 are generated in a process of providing an exercise program.

In one example, a providing apparatus provides an exercise program to a user. In this example, the exercise program may be generated based on an exercise ability or personal information of a user. Also, the exercise program may be provided through, for example, a generally commercialized application. The personal information may include a physical activity coefficient and body information of the user, for example, a gender, an age, a height, a body mass index (BMI), a waist measurement, a hip circumference, a waist hip ratio (WHR), and a blood pressure. Hereinafter, an example of generating a feedback will be described.

A first feedback 310 is generated while a user performs an exercise program.

In one example, the providing apparatus provides a coaching message at a predetermined time interval based on a heart rate measured from the user while the user performs the exercise program. As an example, a first coaching message or a third coaching message may be consecutively provided four times while the user performs a second set of exercises. In this example, the second set of exercises may be provided based on a cycling exercise program and correspond to a level 3. As described above, the first coaching message is a message for reducing a training pace and the third coaching message is a message for increasing the training pace.

When a number of times that a predetermined coaching message is consecutively provided is greater than a preset number of time, for example, three times, the providing apparatus determines that an exercise intensity of the second set of exercises is unsuitable for the user, and thus adjusts the exercise intensity during the training. As such, the first feedback 310 is generated in a process of providing the coaching message at a predetermined time interval based on the heart rate of the user measured during the training, and adjusting the exercise intensity based on the number of times that the coaching message is consecutively provided.

A second feedback 330 is generated after a termination of the exercise program.

In one example, in response to a termination of the second set of exercises corresponding to the level 3 of the cycling exercise program, the providing apparatus calculates a message score and a time score based on, for example, the heart rate measured in the second set of exercises and a coaching message history of the second set of exercises. The providing apparatus may increase the exercise level of the exercise program to a level 5, decrease the exercise level to a level 2, or maintain a current exercise level. The second feedback 330 is generated in a process of changing an exercise level based on a value calculated based on the heart rate, the coaching message history, and other factors. Depending on an example, the providing apparatus may change the exercise program in consideration of an RPE of the user as well as in a procedure of the second feedback 330.

A third feedback 350 is generated based on exercise history information stored in an exercise history database in response to a continuous progress of the exercise program.

The providing apparatus changes the exercise program based on a training effect index obtained based on the training effect information for each set and each level of exercise. The third feedback 350 is generated in a process of changing the exercise program based on the training effect index.

Figure 4:
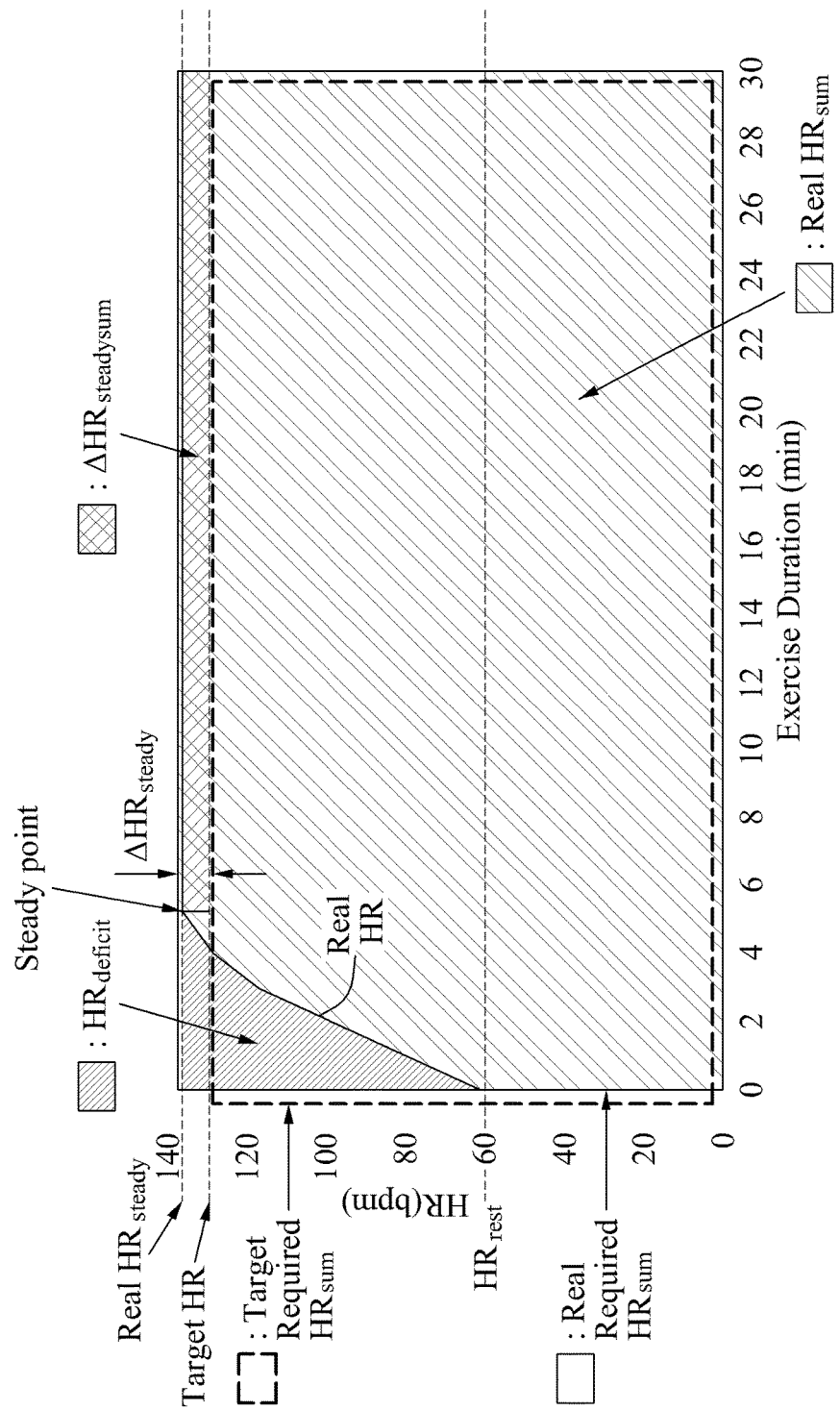
FIG. 4 illustrates an example of a change in a heart rate of a user performing an exercise program.

FIG. 4 illustrates an example of a change in a heart rate of a user performing an exercise program.

A graph of FIG. 4 represents a change in a heart rate of the user measured for about 30 minutes from a starting time of an exercise to a terminating time of the exercise. As shown in the graph, the heart rate does not reach a target heart rate for performing the exercise simultaneously with starting of the exercise. Rather, the heart rate steadily increases for a short period of time until arriving at a steady state. The steady state is a state in which the heart rate of the user remains constant without a significant change after steadily increasing in response to a start of the exercise.

For example, when a user starts to run at a speed of 8 kilometers per hour (km/h), a heart rate may increase from 60 beats per minute (bpm) measured in a rest state. The heart rate increases to an appropriate level for maintaining the speed of 8 km/h, and remains constant in subsequent time intervals without a significant change.

The providing apparatus calculates various parameters related to the heart rate based on a change in the heart rate while the user is performing the exercise program. The providing apparatus adjusts an exercise intensity of the exercise program, changes an exercise level of the exercise program, or changes the exercise program based on the calculated parameters.

Hereinafter, parameters shown in the graph of FIG. 4 will be described.

A measured heart rate Real HR and HR, is a heart rate actually measured the user performs the exercise program.

A target heart rate Target HR and THR, is a predetermined heart rate of the user under an assumption that the user is in a steady state while performing the exercise program. For example, the target heart rate is a heart rate corresponding to a level to be achieved by the user in the steady state to acquire a training effect suggested in the exercise program.

The providing apparatus determines the target heart rate of the user based on input personalized information including, for example, personal information and a goal of an exercise. In this example, the target heart rate may be determined using, for example, the Karvonen formula $THR=(HR_{max}-HR_{rest}) \times \alpha + HR_{rest}$ and a target intensity $\alpha$. A maximum heart rate $HR_{max}$ is a maximum heart rate recommended by the American College of Sports Medicine (ACSM) for an age of the user. The maximum heart rate may be obtained using a formula, for example, $HR_{max}=206.9-(0.67 \times age)$. Also, the target intensity $\alpha$ is used as a criterion of the exercise intensity, and has a value greater than 0 and less than 1, that is, $0<\alpha<1$, depending on a purpose of the exercise of the user.

A heart rate in a rest state $HR_{rest}$ is a stable heart rate measured in the rest state before the user starts to perform the exercise. In the graph of FIG. 4, the stable heart rate $HR_{rest}$ is 60 bpm.

A target cumulative heart rate Target Required $HR_{sum}$ and $THR_{sum}$ is a cumulative heart rate based on the target heart rate. The cumulative heart rate is an accumulation of the target heart rate. The target cumulative heart rate is used as an index for a total amount of aerobic and anaerobic exercises based on the target heart rate. For example, the target cumulative heart rate is determined by multiplying the target heart rate by an exercise duration as shown in Equation 1 below.

$$\text{Target Required } HR_{sum} = \text{Target HR} \times \text{Exercise Duration} \quad (1)$$

A steady-state heart rate Real $HR_{steady}$ is a heart rate obtained when the measured heart rate reaches a steady state interval. The steady-state heart rate may also be determined based on an average heart rate of the steady state interval.

A first cumulative heart rate Real $HR_{sum}$ and $HR_{sum}$ is a sum obtained by accumulating heart rates actually measured from the user during performance of the exercise program. The first cumulative heart rate may include an aerobic/anaerobic metabolism portion aside from an oxygen deficient state, starting from an initiation of the exercise to the steady state. A total amount of exercise actually performed by the user may be determined based on the first cumulative heart rate.

For example, the first cumulative heart rate is determined by obtaining a sum of heart rates measured from a start time of the exercise to an end time of the exercise as shown in Equation 2 below.

$$HR_{sum} = \sum_{i=start}^{end} HRi \quad (2)$$

A cumulative heart rate difference $\Delta HR_{sum}$ is a difference between a target cumulative heart rate and a cumulative sum of heart rates measured while the user performs the exercise program. The cumulative heart rate difference may be used as an assessment index for determining whether an amount of exercise is excessive, maintained, or deficient when compared to an exercise goal after a termination of the exercise program.

For example, the cumulative heart rate difference is determined based on a difference between the target cumulative heart rate of Equation 1 and the first cumulative heart rate of Equation 2 as shown in Equation 3 below.

$$\Delta HR_{sum} = \text{Real } HR_{sum} - THR_{sum} \quad (3)$$

A cumulative heart rate difference rate $\%\Delta HR_{sum}$ is obtained by expressing the cumulative heart rate difference as a relative value. The cumulative heart rate difference rate may be used to compare a training effect of the exercise program to that of another exercise program.

For example, the cumulative heart rate difference rate is determined by dividing the cumulative heart rate difference of Equation 3 by the target cumulative heart rate of Equation 1 as shown in Equation 4 below.

$$\%\Delta HR_{sum} = \frac{\Delta HR_{sum}}{THR_{sum}} \quad (4)$$

The second cumulative heart rate Real Required $HR_{sum}$ is a required cumulative heart rate based on a steady-state heart rate during the actual training. The second cumulative heart rate is used to determine a total amount of aerobic and anaerobic exercises based on the steady-state heart rate. For example, the second cumulative heart rate is obtained by multiplying the exercise duration by the steady-state heart rate as shown in Equation 5 below.

$$\text{Real Required } HR_{sum} = \text{Real } HR_{steady} \times \text{Exercise Duration} \quad (5)$$

$\Delta HR_{steady}$ denotes a difference between the target heart rate Target HR and the steady-state heart rate Real $HR_{steady}$ measured during the actual training as shown in Equation 6 below.

$$\Delta HR_{steady} = \text{Real } HR_{steady} - \text{Target HR} \quad (6)$$

$\Delta HR_{steady}$ may be used as an assessment index for determining whether an actual amount of exercise is excessive, maintained, or deficient when compared to an exercise goal set for the user.

$\Delta HR_{steadysum}$ denotes a sum of $\Delta HR_{steady}$. $\Delta HR_{steadysum}$ is determined by obtaining the sum of $\Delta HR_{steady}$ from a steady point, which is a time at which the steady time starts, to an exercise termination time as shown in Equation 7 below.

$$\Delta HR_{steadysum} = \sum_{i=steady\ point}^{end} \Delta HR_{steady} \quad (7)$$

$\Delta HR_{steadysum}$ may be used as an assessment index for determining whether an actual amount of exercise performed after the steady state is excessive, maintained, or deficient when compared to the exercise goal after the user terminates the exercise program. $\Delta HR_{steadysum}$ is obtained based on the heart rate measured in a steady state interval, and thus a portion related to an aerobic exercise may be applied to $\Delta HR_{steadysum}$.

A heart rate of an anaerobic metabolism area $HR_{deficit}$ is a difference between the second cumulative heart rate and the first cumulative heart rate as shown in Equation 8 below. An anaerobic metabolism area is a portion in which the exercise is performed through an anaerobic metabolism instead of an aerobic metabolism. The anaerobic metabolism area may be applied to the heart rate of the anaerobic metabolism area.

$$HR_{deficit} = \text{Real Required } HR_{sum} - HR_{sum} \quad (8)$$

$HR_{deficit}$ may be used to as a assessment index to determine a degree to which an anaerobic metabolism is applied during the training. The providing apparatus may determine the ratio of the heart rate of the anaerobic metabolism area to the second cumulative heart rate to be a rate of the anaerobic metabolism applied in a training interval. A rate of the aerobic metabolism applied in the training interval may be obtained by subtracting the rate of the anaerobic metabolism from a total rate.

The providing apparatus calculates an anaerobic energy consumption rate $\%\Delta HR_{deficit}$ based on the second cumulative heart rate and the first cumulative heart rate as shown in Equation 9 below.

$$\% \ HR_{deficit} = \frac{HR_{deficit}}{\text{Real Required } HR_{sum}} \times 100 \quad (9)$$
$$= \frac{(\text{Real Required } HR_{sum} - HR_{sum})}{\text{Real Required } HR_{sum}} \times 100$$

% $HR_{deficit}$ is obtained based on a contrast ratio between the second cumulative heart rate and a heart rate of the anaerobic metabolism area measured before the steady state while the exercise is actually performed.

Hereinafter, an example of the providing apparatus calculating various parameters related to the heart rate based on heart rate information illustrated in the graph of FIG. 4 will be described. An exercise managing method is described based on an example in which a user runs and a target heart rate of the user is set to 134 bpm. An exercise duration recommended to the user is 30 minutes and the user reaches the steady state at a time at which a 5 minute period elapses from a start of the exercise. The providing apparatus calculates various parameters related to the heart rate as follows.

(1) Target heart rate THR=134 bpm
(2) Target cumulative heart rate $THR_{sum}$ in exercise duration=134 bpm×30 minutes ×60 seconds=241,200 beats The target cumulative heart rate is determined by multiplying the target heart rate by the exercise duration as shown in Equation 1, and is calculated based on a unit of seconds.

(3) Heart rate in steady stage during actual training $HR_{steady}$ 137.4 bpm

An exercise intensity of the actual training is applied to the steady-state heart rate. In a case in which the user reaches the steady state within 5 minutes from the start of the exercise, the providing apparatus determines an average heart rate calculated in the steady state interval after 5 minutes to be the steady-state heart rate.

(4) Second cumulative heart rate Real Required $HR_{sum}$:
137.4 bpm×30 minutes×60 seconds=247,320 beats The providing apparatus calculates the second cumulative heart rate for the exercise duration based on the steady-state heart rate and Equation 5.

Figure 5:
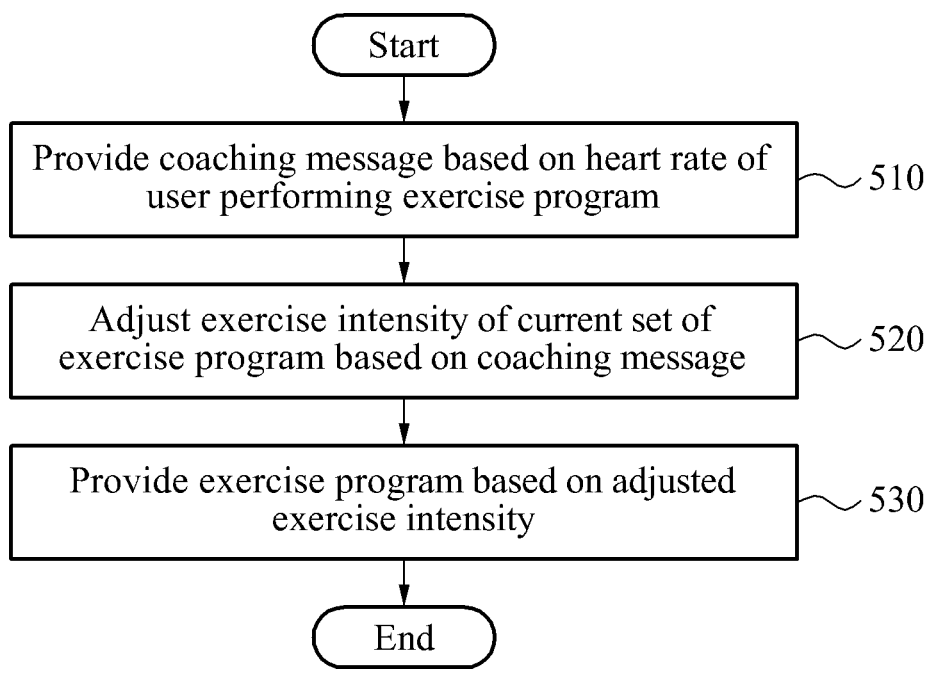
FIG. 5 illustrates another example of a method of providing an exercise program.

FIG. 5 illustrates another example of a method of providing an exercise program.

Referring to FIG. 5, in operation 510, a providing apparatus provides a coaching message based on a heart rate of a user performing an exercise program. The coaching message is a message for coaching a training pace of the exercise program. As described above, a first coaching message, a second coaching message, a third coaching message, and an alert message may be provided at a predetermined time interval as the coaching message.

In operation 520, the providing apparatus adjusts an exercise intensity of a current set of the exercise program based on the coaching message provided in operation 510.

In operation 530, the providing apparatus provides the exercise program based on the exercise intensity adjusted in operation 520. A method in which the providing apparatus provides the coaching message and adjusts the exercise intensity in the current set will be described with reference to FIG. 7.

Figure 6:
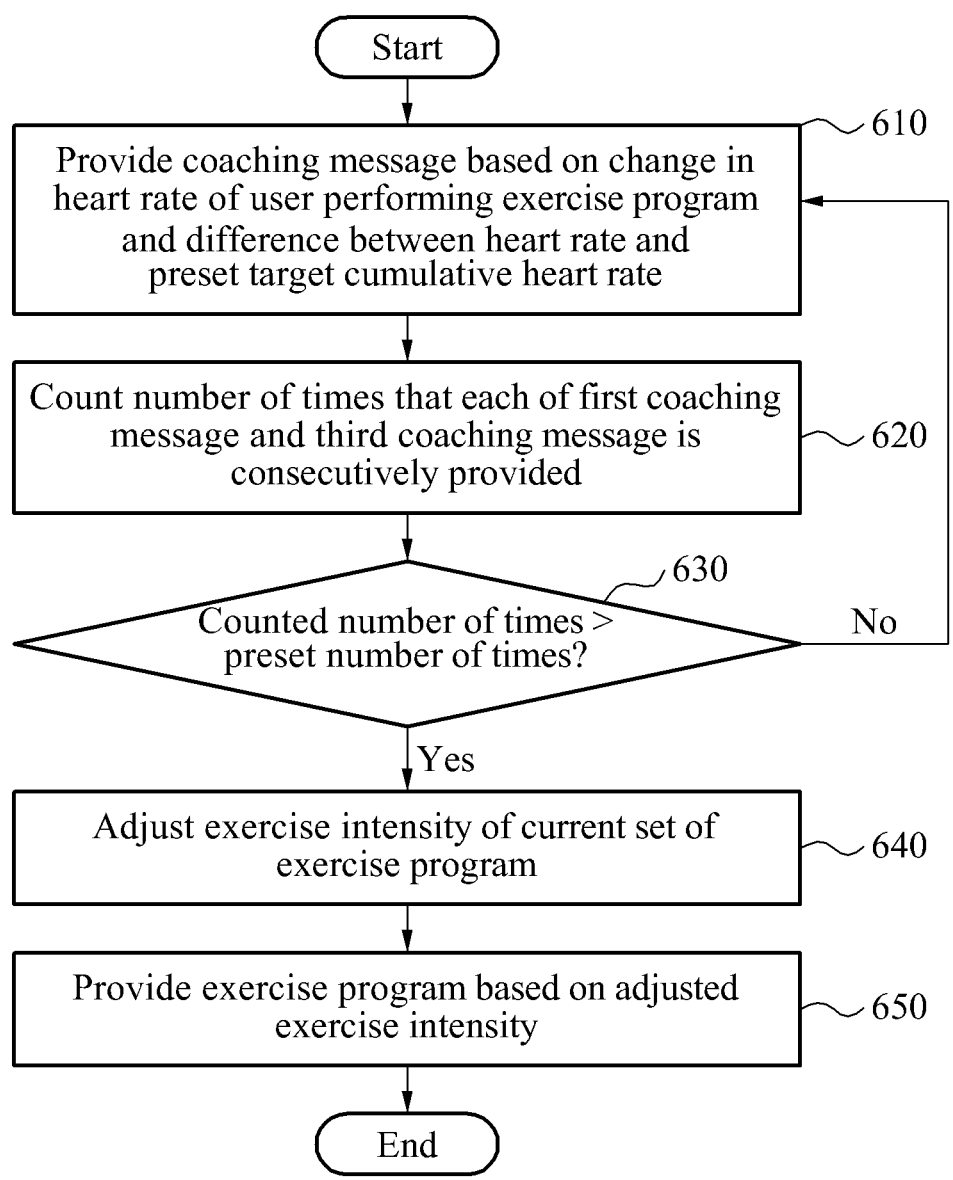
FIG. 6 illustrates another example of a method of providing an exercise program.

FIG. 6 illustrates another example of a method of providing an exercise program.

Referring to FIG. 6, in operation 610, a providing apparatus provides one of a first coaching message, a second coaching message, and a third coaching message based on a change in a heart rate of a user performing an exercise program and a difference between the heart rate and a preset target cumulative heart rate.

In operation 620, the providing apparatus counts a number of times that each of the first coaching message and the third coaching message is consecutively provided. The first coaching message is a message for reducing a training pace and the third coaching message is a message for increasing the training pace.

In operation 630, the providing apparatus determines whether the number of times counted in operation 620 is greater than a preset number of times, for example, three times.

When the counted number of times is determined to be less than or equal to the preset number of times in operation 630, the providing apparatus returns to operation 610.

When the counted number of times is determined to be greater than the preset number of times in operation 630, the providing apparatus adjusts an exercise intensity of a current set in operation 640. In one example, the providing apparatus increases the exercise intensity of the current set when the first coaching message is consecutively provided four times, reduces the exercise intensity of the current set when the third coaching message is consecutively provided four times.

In operation 650, the providing apparatus provides the exercise program based on the exercise intensity adjusted in operation 640.

Figure 7:
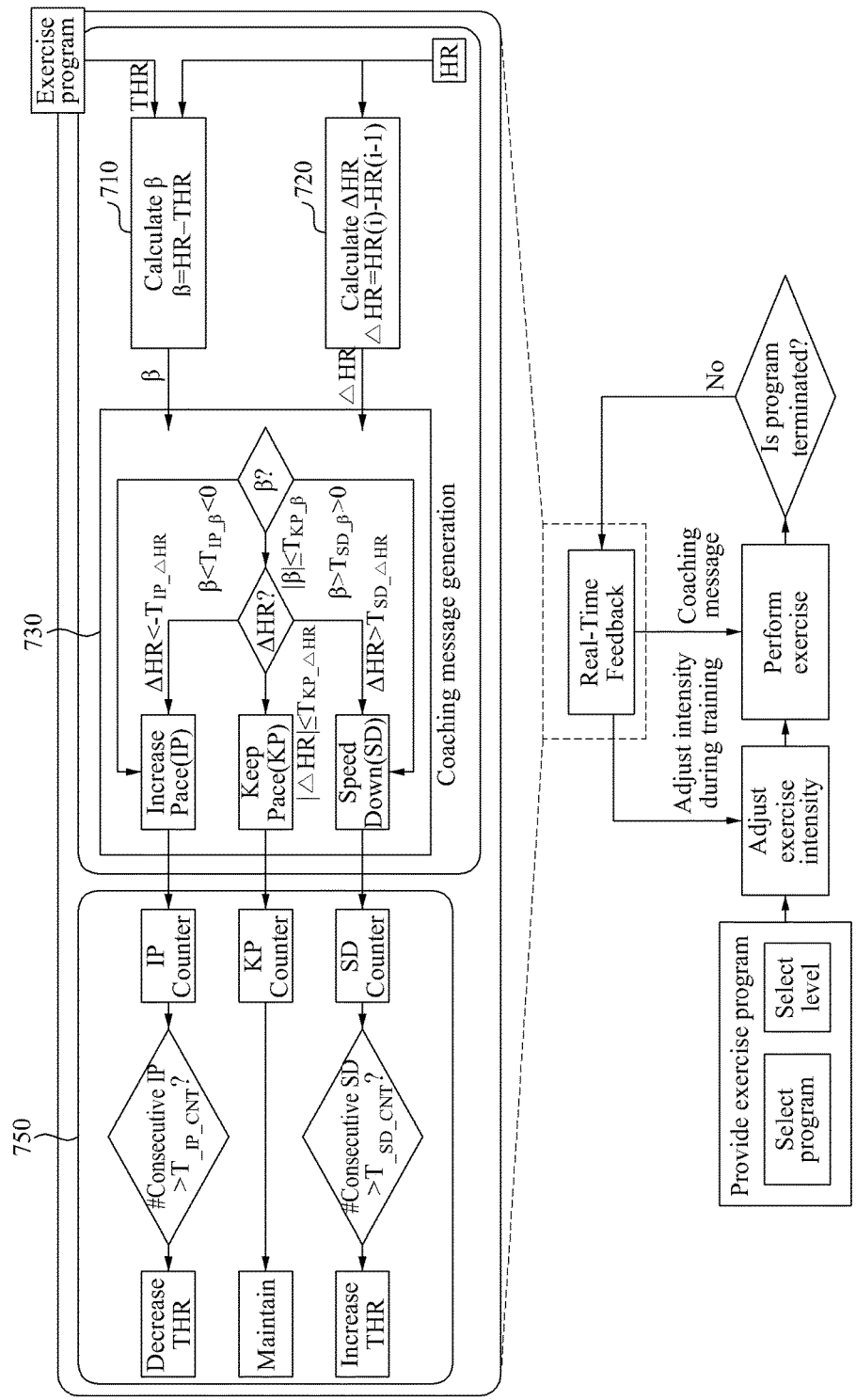
FIG. 7 illustrates an example of a method of providing an exercise program based on a feedback while the exercise program is being performed.

FIG. 7 illustrates an example of a method of providing an exercise program based on a feedback while the exercise program is being performed.

FIG. 7 illustrates an example of a method in which a providing apparatus provides a different coaching messages based on a feedback during an exercise, and a method in which the providing apparatus adjusts an exercise intensity of an exercise program based on a coaching message.

In operation 710, the providing apparatus receives a preset target heart rate THR based on, for example, an exercise program and receives a heart rate HR measured from a user, and calculates a difference between the preset target cumulative heart rate and the measured heart rate β=HR−THR. In operation 720, the providing apparatus calculates a variation in the heart rate ΔHR=HR(i)−HR(i−1), i being a natural number greater than or equal to 1.

In operation 730, the providing apparatus generates a coaching message based on the difference β between the target heart rate and the measured heart rate and the variation ΔHR in the heart rate.

In operation 730, the providing apparatus compares the difference β to a preset threshold $T_β$, for example, 6 bpm, and then compares the variation ΔHR to a preset threshold $T_{ΔHR}$. The threshold $T_β$ for the difference β may be set to have the same value $T_β$ for each coaching message, or may be set to have different values $T_{IP\_β}$, $T_{KP\_β}$, and $T_{SD\_β}$ for each coaching message. Similarly, the threshold $T_{ΔHR}$ for the variation ΔHR to have the same value $T_{ΔHR}$ for each coaching message, or may be set to have different values $T_{IP\_ΔHR}$, $T_{KP\_ΔHR}$, and $T_{SD\_ΔHR}$ for each coaching message.

In response to a determination that the heart rate of the user is lower than the target heart rate corresponding to a current exercise intensity, for example, β<−6 bpm<0, the providing apparatus generates a third coaching message indicating "increase pace (IP)" for increasing a training pace.

In response to a determination that the heart rate of the user is higher than the target heart rate corresponding to the current exercise intensity, for example, β>6 bpm>0, the providing apparatus generates a first coaching message indicating "speed down (SD)" for reducing the training pace.

In response to a determination that the heart rate of the user is appropriate for the target heart rate corresponding to the current exercise intensity, for example, −6 bpm≤β≤6 bpm, the providing apparatus compares the variation ΔHR to the threshold $T_{\Delta HR}$.

As an example, when the variation ΔHR<−$T_{\Delta HR}$, the providing apparatus generates the third coaching message for increasing the current exercise intensity. When an absolute value |ΔHR| of the variation ΔHR≤$T_{\Delta HR}$, the providing apparatus generates a second coaching message indicating "keep pace (KP)" for maintaining the current exercise intensity. When the variation ΔHR>$T_{\Delta HR}$, the providing apparatus generates the first coaching message for reducing the current exercise intensity.

In operation 750, the providing apparatus adjusts the exercise intensity based on the coaching message generated in operation 730.

The providing apparatus provides the coaching message generated in operation 730 to a mobile device or a wearable device, and then counts a number of times that each coaching message is provided in operation 750 using counter IP Counter, KP counter, and SD counter. The providing apparatus counts the number of times that each of the first coaching message and the third coaching message is consecutively provided, and compares the counted number of times to a preset number of times $T_{\_CNT}$. In this example, the preset number of times $T_{\_CNT}$ is set to be $T_{\_SD\_CNT}$ for the first coaching message and $T_{\_IP\_CNT}$ for the third coaching message. Alternatively, the preset number of times $T_{\_CNT}$ may be set to be the same for the first coaching message and the third coaching message.

When the number of times that the first coaching message is consecutively provided is greater than the preset number of times $T_{\_SD\_CNT}$, the providing apparatus increases an exercise intensity of a current set. The providing apparatus increases the exercise intensity by, for example, increasing the target heart rate. The foregoing example is based on a case in which the target heart rate is lower than the measured heart rate. As an example, the user may keep a relatively high exercise intensity even though the first coaching message is repetitively provided to reduce the training pace. In this example, the providing apparatus determines that a strength and an exercise ability of the user are higher than a predicted level, and thus increases the exercise intensity.

When the number of times that the third coaching message is consecutively provided is greater than the preset number of times $T_{\_IP\_CNT}$, the providing apparatus reduces the exercise intensity of the current set. The providing apparatus reduces the exercise intensity by, for example, reducing the target heart rate. The foregoing example is based on a case in which the target heart rate is higher than the measured heart rate. As an example, the user may keep a relatively low exercise intensity even though the third coaching message is repetitively provided to increase the training pace. In this example, the providing apparatus determines that a strength and an exercise ability of the user are lower than a predicted level, and thus reduces the exercise intensity.

Depending on an example, when an excess of the exercise intensity is determined to be greater than a predetermined threshold, or when the variation in the heart rate of the user rapidly increases, the providing apparatus may provide an alert message to the user.

Figure 8A:
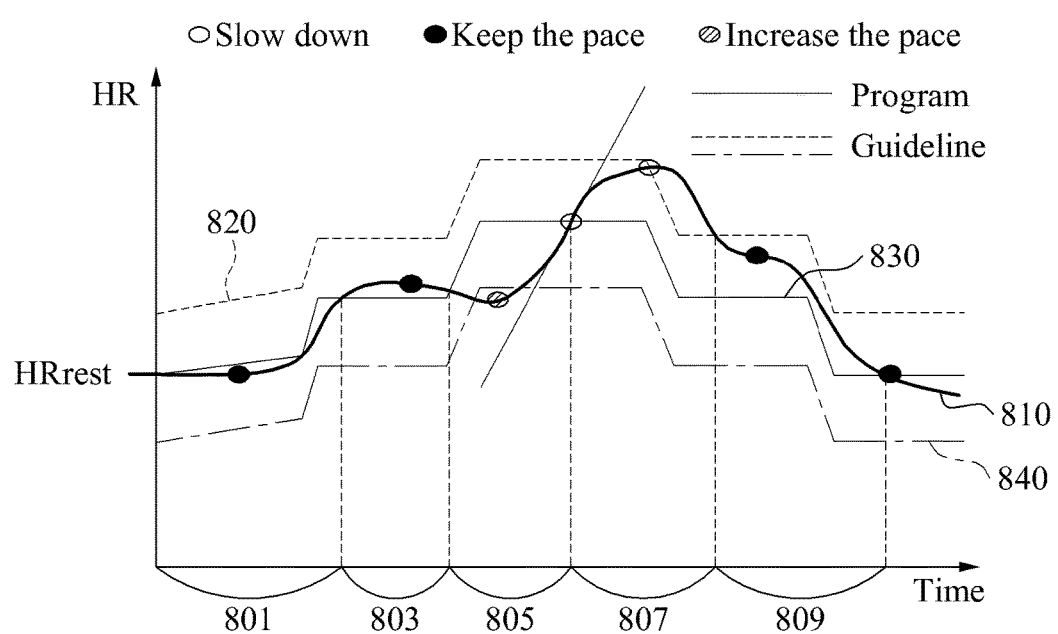
FIGS. 8A and 8B illustrate an example of a method of providing different coaching messages based on feedback while an exercise program is being performed and a method of analyzing for a feedback after a termination of the exercise program.
Figure 8B:
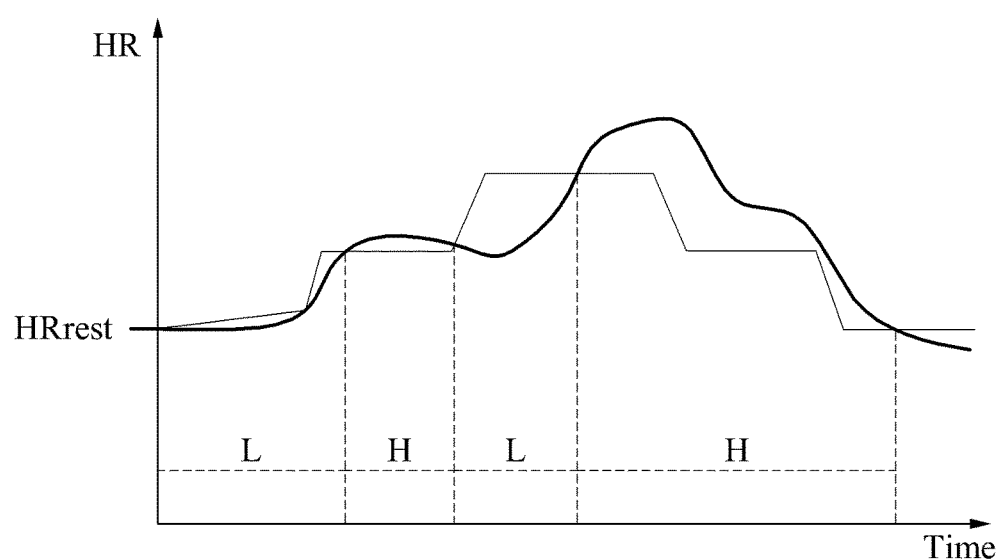

FIGS. 8A and 8B illustrate an example of a method of providing different coaching messages based on a feedback while an exercise program is being performed and a method of analyzing for a feedback after a termination of the exercise program.

FIG. 8A illustrates an example in which different coaching messages are provided based on a heart rate of a user measured during a training of an exercise program.

In FIG. 8A, a curve 810 represents an actual heart rate of the user measured while the user performs the exercise program. A curve 830 represents a target heart rate corresponding to an exercise intensity of the exercise program. A curve 820 represents an upper guideline for the target heart rate of the exercise program. A curve 840 represents a lower guideline for the target heart rate. The curve 820 and the curve 840 may be determined based on a threshold for a difference between the target heart rate and the heart rate of the user. Points included in the curve 810 indicate a type of coaching message provided by a providing apparatus at a corresponding time.

A time interval 801 is an interval in which the heart rate of the user is lower than the target heart rate and a difference between the heart rate and the target heart rate is less than or equal to a threshold. A time interval 803 is an interval in which the heart rate of the user is higher than the target heart rate and the difference between the heart rate and the target heart rate is less than or equal to a threshold. The providing apparatus provides a second coaching message for maintaining a training pace in the time interval 801 and the time interval 803.

A time interval 805 includes a time during which the heart rate of the user is lower than the lower guideline for the target heart rate and a time during which the heart rate rapidly increases to exceed a predetermined level. The providing apparatus provides a third coaching message for increasing the training pace when the heart rate of the user is lower than the lower guideline for the target heart rate in the time interval 805. Also, the providing apparatus provides a first coaching message for reducing the training pace when the heart rate rapidly increases to exceed a predetermined level in the time interval 805.

A time interval 807 is an interval in which the heart rate of the user rapidly increases to reach the upper guideline and then decreases. The providing apparatus provides the first coaching message for reducing the training pace when the heart rate of the user reaches the upper guideline in the time interval 807. Through this, the providing apparatus may prevent an incident such as an arrhythmia and a heart failure due to a sudden high-intensity exercise.

A time interval 809 is an interval in which the heart rate of the user is higher than the target heart rate and steadily decreases within the higher guideline. The providing apparatus provides the second coaching message for maintaining the training pace.

FIG. 8B illustrates an example of an analysis result for providing an after-exercise feedback based on an exercise program.

In FIG. 8B, L denotes a time during which an actually measured heart rate HR is lower than a target heart rate THR, that is, $T_{Low}$=Time (HR<THR), and H denotes a time during which the actually measured heart rate HR is higher than the target heart rate THR, that is, $T_{High}$=Time (HR>THR). For example, an interval L indicates a time during which a heart rate measured in a current set of exercises is lower than a preset target heart rate, and an interval H indicates a time during which the heart rate measured in the current set of exercises is higher than the preset target heart rate.

The time intervals 801 and 805 of FIG. 8A correspond to the intervals L of FIG. 8B, and the time intervals 803, 807, and 809 of FIG. 8A correspond to the intervals H of FIG. 8B. The providing apparatus calculates a time score used to change an exercise level in response to the after-exercise feedback based on the intervals L and the intervals H.

Figure 9:
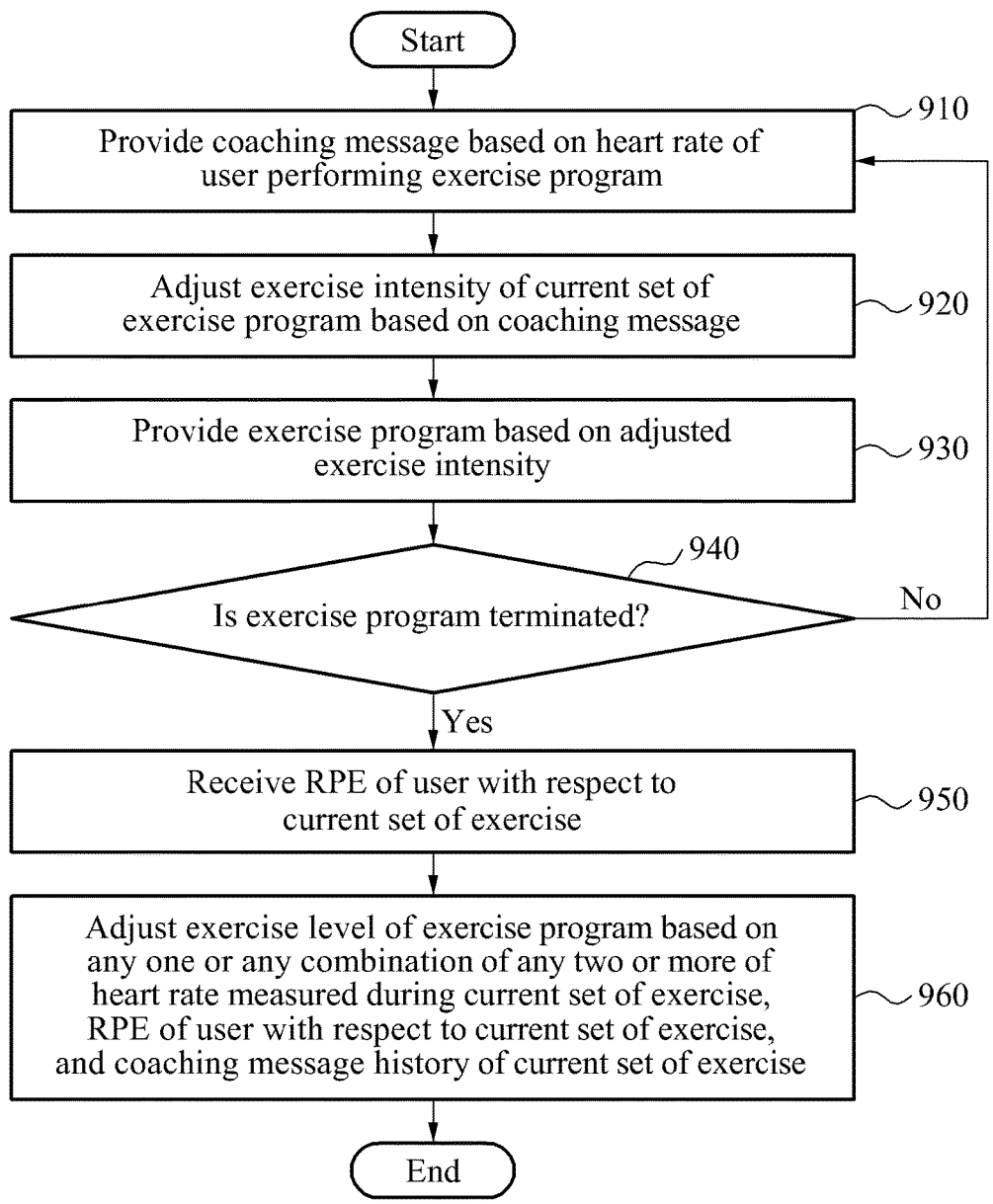
FIG. 9 illustrates another example of a method of providing an exercise program.

FIG. 9 illustrates another example of a method of providing an exercise program.

Referring to FIG. 9, in operation 910, a providing apparatus provides a coaching message based on a heart rate of a user performing an exercise program. In operation 920, the providing apparatus adjusts an exercise intensity of a current set of the exercise program based on the coaching message provided in operation 910.

In operation 930, the providing apparatus provides the exercise program based on the exercise intensity adjusted in operation 920.

In operation 940, the providing apparatus determines whether the exercise program has terminated. In this example, the providing apparatus determines whether an exercise of the current set has terminated.

When it is determined that the exercise program has not terminated in operation 940, the providing apparatus returns to operation 910.

When it is determined that the exercise program has terminated in operation 940, the providing apparatus receives an RPE of a user with respect to the exercise of the current set in operation 950. Although the RPE is a value autonomously input by the user, the RPE has a tendency of being proportional to the exercise intensity when values of the RPE are accumulated. The RPE and the heart rate of the user may have a relationship, for example, RPE=0.72+ 0.081×HR, HR being the heart rate.

In one example, when only one of the heart rate and the RPE is known, the aforementioned relationship may be used to estimate an unknown value. Depending on an example, the providing apparatus may estimate the RPE based on the heart rate of the user irrespective of whether the user inputs the RPE.

In operation 960, the providing apparatus adjusts an exercise level of the exercise program based on any one or any combination of any two or more of a heart rate measured during a current set of exercises, an RPE of the user with respect to the current set of exercises, and a coaching message history of the current set.

A method in which the providing apparatus adjusts the exercise level of the exercise program will be described with reference to FIG. 10.

Figure 10:
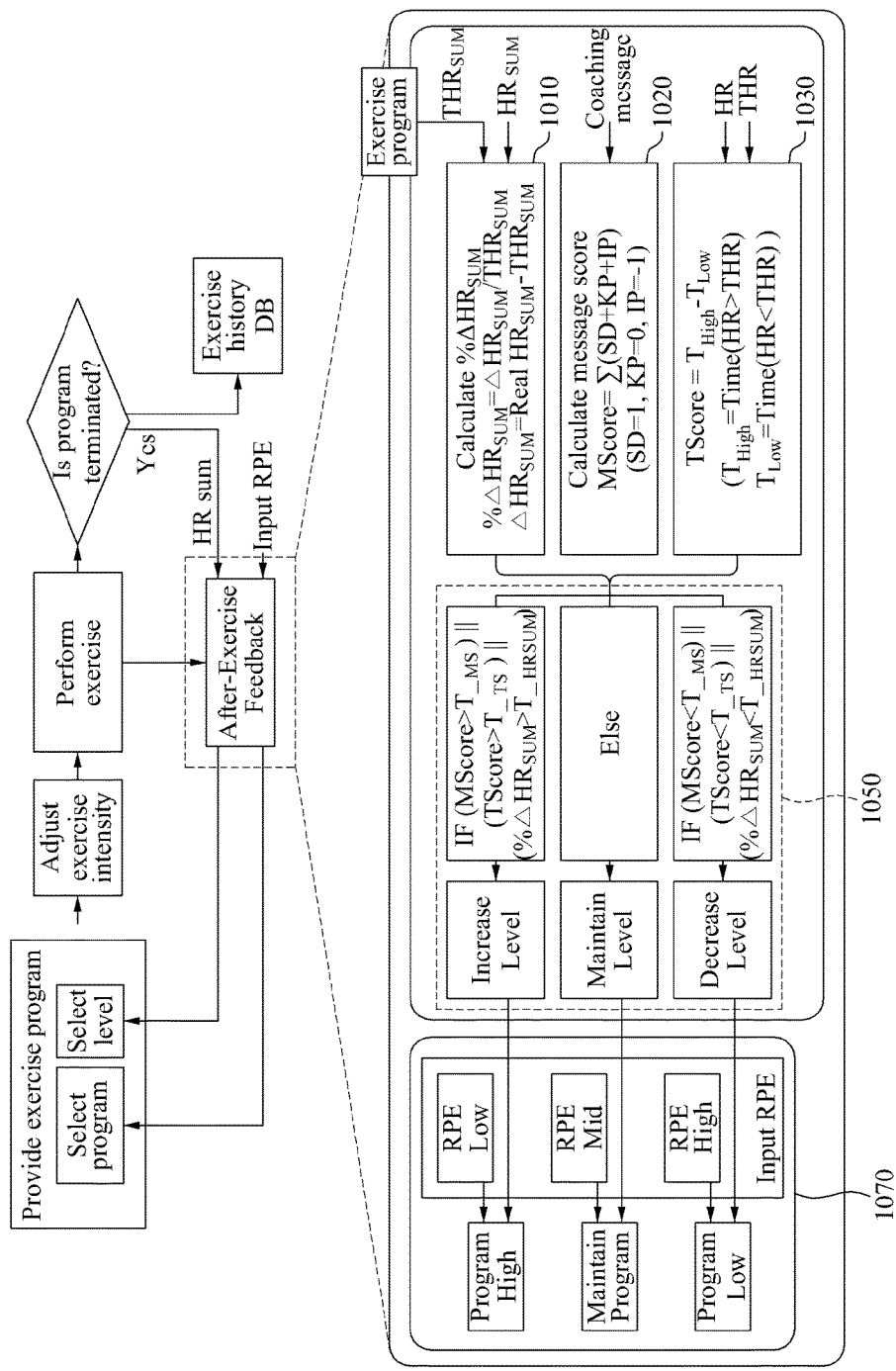
FIG. 10 illustrates a method of adjusting an exercise level of an exercise program based on a feedback after a termination of the exercise program.

FIG. 10 illustrates a method of adjusting an exercise level of an exercise program based on a feedback after a termination of the exercise program.

Referring to FIG. 10, a providing apparatus adjusts an exercise level of an exercise program based on a feedback after an exercise.

In operation 1010, the providing apparatus calculates a cumulative heart rate difference rate %ΔHR$_{sum}$ using a first cumulative heart rate HR$_{SUM}$ based on a heart rate HR measured during a current set of exercises and a preset target cumulative heart rate THR$_{SUM}$ based on a preset target heart rate THR. The cumulative heart rate difference rate %ΔHR$_{SUM}$ is calculated using Equation 4 as described above.

In operation 1020, the providing apparatus calculates a message score MScore based on a coaching message history. The providing apparatus calculates the message score using Equation 10 below in which a preset weight is applied to each coaching message included in the coaching message history.

$$MScore = \Sigma(\alpha SD + \beta KP + \gamma IP) \quad (10)$$

In Equation 10, SD denotes a first coaching message, KP denotes a second coaching message, IP denotes a third coaching message, α denotes a weight applied to the first coaching message, β denotes a weight applied to the second coaching message, and γ denotes a weight applied to the third coaching message.

For example, α may be 0.5, β may be 0, and γ may be −1.5.

In operation 1030, the providing apparatus calculates a time score TScore based on a time T$_{High}$ during which the heart rate measured in the current set of exercises is higher than a preset target heart rate and a time T$_{Low}$ during which the measured heart rate is lower than the preset target heart rate. The time score is calculated using Equation 11 below.

$$TScore = T_{High} - T_{Low} \quad (11)$$

As described in an example of FIG. 8B, T$_{Low}$ denotes the time during which the measured heart rate is lower than the preset target heart rate, that is, HR<THR, and T$_{High}$ denotes the time during which the measured heart rate is higher than the preset target heart rate, that is, HR>THR.

In operation 1050, the providing apparatus adjusts an exercise level of the exercise program based on any one or any combination of any two or more of the calculated cumulative heart rate difference rate, the message score, and the time score. In this example, the providing apparatus adjusts the exercise level of the exercise program using Equation 12 below.

$$\text{If}(MScore > T\_{MS}) || (TScore > T\_{TS}) || (\%\Delta HR_{sum} > T_{HRSUM}) \quad (12)$$

then Increase Level

If(MScore < T_{MS})

$$|| (TScore < T\_{TS}) || (\%\Delta HR_{SUM} < T_{HRSUM})$$

then Decrease Level else

Maintain Level

In Equation 12, T$_{\_MS}$ denotes a threshold of the message score, T$_{\_MS}$ denotes a threshold of the time score, and T$_{\_HRSUM}$ denotes a threshold of the cumulative heart rate difference rate.

Equation 12 expresses a degree to which the user appropriately performs the exercise program. For example, the time score and the message score of Equation 12 are indexes for assessing a training conformance. A high conformance index indicates that the exercise program is suitable for the user and the user is effectively performs the exercise program.

In operation 1070, the providing apparatus changes the exercise program based on the RPE of the user and any one or any combination of any two or more of the cumulative heart rate difference rate, the message score, and the time score. When a message for increasing, maintaining, or reducing the exercise level of the exercise program is provided in operation 1050, the providing message changes the exercise program based on the RPE of the user in addition to the message.

In an example, as a result of operation 1050, when the exercise level of the exercise program is determined to be increased, and when the RPE of the user with respect to the exercise program is relatively low, the providing apparatus changes the exercise program to another program having a higher exercise intensity in operation 1070.

In another example, as a result of operation 1050, when the exercise level of the exercise program is determined to be reduced, and when the RPE of the user with respect to the exercise program is relatively high, the providing apparatus changes the exercise program to another program having a lower exercise intensity in operation 1070.

In another example, as a result of operation 1050, when the exercise level of the exercise program is determined to be maintained, and when the RPE of the user with respect to the exercise program is approximately intermediate, the providing apparatus maintains the exercise program in operation 1070.

Figure 11:
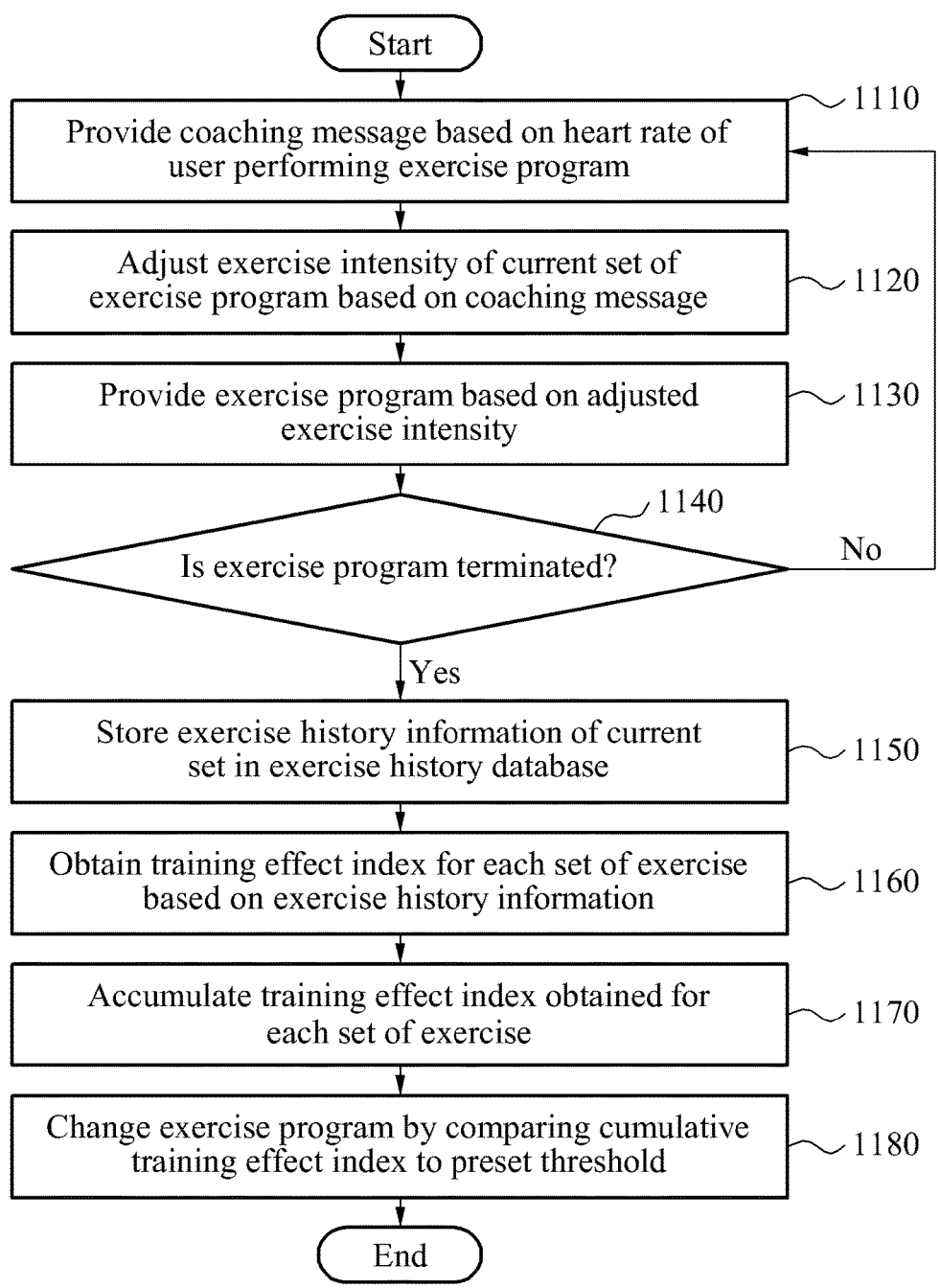
FIG. 11 illustrates another example of a method of providing an exercise program.

FIG. 11 illustrates another example of a method of providing an exercise program.

Referring to FIG. 11, in operation 1110, a providing apparatus provides a coaching message based on a heart rate of a user performing an exercise program. In operation 1120, the providing apparatus adjusts an exercise intensity of a current set of the exercise program based on the coaching message provided in operation 1110.

In operation 1130, the providing apparatus provides the exercise program based on the exercise intensity adjusted in operation 1120.

In operation 1140, the providing apparatus determines whether the exercise program has terminated. In this example, the providing apparatus determines whether an exercise of the current set has terminated. When it is determined that the exercise program has not terminated in operation 1140, the providing apparatus returns to operation 1110.

When it is determined that the exercise program has terminated in operation 1140, the providing apparatus stores exercise history information of the current set in an exercise history database in operation 1150. The exercise history information includes, for example, a training result, a heart rate measured during an exercise, an RPE of the user with respect to the exercise, and a coaching history based on a coaching message history of the coaching messages provided in operation 1110.

In operation 1160, the providing apparatus obtains a training effect index for each set of exercises based on the exercise history information stored in the exercise history database. The training effect index includes, for example, a first training effect index indicating a qualitative evaluation result of the training performed based on the exercise program and a second training effect index indicating a quantitative evaluation result of the training performed based on the exercise program.

In operation 1170, the providing apparatus accumulates the training effect index obtained for each set of exercises in the exercise program in operation 1160 to obtain a cumulative training effect index. In operation 1180, the providing apparatus changes the exercise program by comparing the cumulative training effect index to a preset threshold. The providing apparatus changes the exercise program using one of the first training effect index and the second training effect index. Alternatively, the providing apparatus changes the exercise program based on a result of combining the first training effect index and the second training effect index.

A method in which the providing apparatus obtains the training effect index and a method in which the providing apparatus changes the exercise program will be described with reference to FIG. 12.

FIG. 12 illustrates an example of a method of changing an exercise program using a feedback based on a training history of the exercise program.

Referring to FIG. 12, in operation 1210, a providing apparatus calculates a cumulative heart rate difference rate %$\Delta HR_{SUM}$ using a preset target cumulative heart rate $THR_{SUM}$ and a first cumulative heart rate $HR_{SUM}$ based on a heart rate measured during a current set of exercises. The cumulative heart rate difference rate %$\Delta HR_{SUM}$ is calculated using Equation 4 as described above.

In operation 1220, the providing apparatus calculates an anaerobic energy metabolism consumption rate %$\Delta HR_{deficit}$ using the first cumulative heart rate $HR_{SUM}$ and a second cumulative heart rate Real Required $HR_{SUM}$. The anaerobic energy metabolism consumption rate %$\Delta HR_{deficit}$ is calculated using Equation 9 as described above.

In operation 1230, the providing apparatus obtains a first training effect index using the cumulative heart rate difference rate calculated in operation 1210. The first training effect index is used as an index indicating a qualitative assessment result of an exercise performed based on the exercise program.

The providing apparatus also obtains the first training effect index using, for example, the cumulative heart rate difference rate and a target heart rate, $THR_{HS}$, of the current set of exercises.

As an example, when the cumulative heart rate difference rate is lower than $T_{\_HS1}$ indicating a target heart rate of a first set of exercises, that is, %$\Delta HR_{SUM} < T_{\_HS1}$, the providing apparatus scores 1 point on the first training effect index. When $T_{\_HS2\_LOW} < $ %$\Delta HR_{SUM} < T_{\_HS2\_HIGH}$, the providing apparatus scores 2 points on the first training effect index. When $T_{\_HS3\_LOW} < $ %$\Delta HR_{SUM} < T_{\_HS3\_HIGH}$, the providing apparatus scores 3 points on the first training effect index. When $T_{\_HS4\_LOW} < $ %$\Delta HR_{SUM} < T_{\_HS4\_HIGH}$, the providing apparatus scores 4 points on the first training effect index. When the cumulative heart rate difference rate is higher than a target heart rate of a fifth set of exercises, that is, %$\Delta\Delta HR_{sum} > T_{\_HS5}$, the providing apparatus scores 5 points on the first training effect index. $T_{\_HSK}$ denotes a threshold for identifying a first exercise training effect index for a K-th set of exercises.

In operation 1240, the providing apparatus obtains a second training effect index based on the anaerobic energy metabolism consumption rate calculated in operation 1220. The second training effect index is used as an index indicating a quantitative assessment result of the exercise performed based on the exercise program. The providing apparatus obtains the second training effect index by comparing the anaerobic energy metabolism consumption rate to a preset threshold.

As an example, when the anaerobic energy metabolism consumption rate % $HR_{deficit}$ is less than a threshold $T_{\_HD1}$, that is, % $HR_{deficit} < T_{\_HD1}$, the providing apparatus scores 1 point on the second training effect index. When $T_{\_HD2\_LOW} < $ % $HR_{deficit} < T_{\_HD2\_HIGH}$, the providing apparatus scores 2 points on the second training effect index. When $T_{\_HD3\_LOW} < $ % $HR_{deficit} < T_{\_HD3\_HIGH}$, the providing apparatus scores 3 points on the second training effect index. When $T_{\_HD4\_LOW} < $ % $HR_{deficit} < T_{\_HD4\_HIGH}$, the providing apparatus scores 4 points on the second training effect index. When the anaerobic energy metabolism consumption rate is greater than a threshold $T_{\_HD5}$, that is, % $HR_{deficit} > T_{\_HD5}$, the providing apparatus scored 5 on the second training effect index. $T_{\_HDK}$ denotes a threshold for identifying a second training effect of the K-th set of exercises. Depending on an example, $T_{\_HDK}$ may be the same as $T_{\_HSK}$, or may be different from $T_{\_HSK}$.

In operation 1250, the providing apparatus changes the exercise program by calculating a first cumulative training effect index and a second cumulative training effect index for each set of exercises in the exercise program, comparing the first cumulative training effect index to a first preset threshold $T_{\_TE1}$, and comparing the second cumulative training effect index to a second preset threshold $T_{\_TE2}$. The providing apparatus calculates the first cumulative training effect index by accumulating the first training effect index obtained for each set of exercises in the exercise program in operation 1230, and calculates the second cumulative training effect index by accumulating the second training effect index obtained for each set of exercises in the exercise program in operation 1240.

The providing apparatus changes a current exercise program to a higher strength exercise program when the first cumulative training effect index is greater than the first preset threshold $T_{\_TE1}$ and the second cumulative training effect index is greater than the second preset threshold $T_{\_TE2}$.

The providing apparatus changes the current exercise program to a lower strength exercise program when the first cumulative training effect index is less than or equal to the first preset threshold and the second cumulative training effect index is less than or equal to the second preset threshold $T_{\_TE2}$.

The providing apparatus maintains the current exercise program unchanged when the first cumulative training effect index is greater than the first preset threshold and the second cumulative training effect index is less than or equal to the second preset threshold $T_{\_TE2}$.

The providing apparatus also maintains the current exercise program unchanged when the first cumulative training effect index is less than or equal to the first preset threshold $T_{\_TE1}$ and the second cumulative training effect index is greater than the second preset threshold $T_{\_TE2}$.

Depending on an example, the providing apparatus may also estimate a heart rate corresponding to an RPE of a user or the RPE corresponding to the heart rate of the user based on an exercise history database including cumulative information related to previous sets of exercises when a measurer measuring the heart rate of the user is absent or the RPE of the user is not input. The RPE of the user may be expressed as, for example, a function of a heart rate HR of the user as described above with reference to FIG. 9.

When the heart rate is not measured by a wearable device, the providing apparatus may estimate the heart rate or a change in the heart rate based on the RPE of the user stored in the exercise history database using, for example, a regression analysis such as a linear regression analysis, a multi-layer perceptron, or a neural network.

The apparatus 100 for providing an exercise program, the measurer 103, and the processor 106 illustrated in FIG. 1A, the wearable device 110 and the mobile device 130 illustrated in FIG. 1B, the wearable device 210, the measurer 213, the processor 233, the mobile device 230, the memory 231, the processor 233, the user interface 235, the guider 237, and the wireless module 241 illustrated in FIG. 2 that perform the operations described herein with respect to FIGS. 1A-12 are implemented by hardware components. Examples of hardware components include controllers, sensors, generators, drivers, memories, comparators, arithmetic logic units, adders, subtractors, multipliers, dividers, integrators, and any other electronic components known to one of ordinary skill in the art. In one example, the hardware components are implemented by one or more processors or computers. A processor or computer is implemented by computing hardware, for example, by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 1A-12. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 3, 5-7, and 9-12 that perform the operations described herein with respect to FIGS. 1A-12 are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of providing an adjustable exercise program, the method employing a heart rate sensor worn by a user during performance of the exercise program, and a processor in communication with the sensor and configured to provide a coaching message to the user and adjust the exercise program, the method comprising:
providing, by the processor, a coaching message to the user to coach a training pace in the exercise program based on a heart rate, detected by the heart rate sensor, of a user performing the exercise program;
adjusting, by the processor, an exercise intensity of a current set of exercises of the exercise program based on the coaching message; and
providing, by the processor, the exercise program based on the adjusted exercise intensity,
wherein the coaching message is any one or any combination of any two or more of a first coaching message for reducing the training pace, a second coaching message for maintaining the training pace, and a third coaching message for increasing the training pace, and
wherein the adjusting comprises counting a number of times that each of the first coaching message and the third coaching message is consecutively provided, and adjusting the exercise intensity of the current set of exercises in response to a result of the counting being greater than a preset number of times.

2. The method of claim 1, wherein the providing the coaching message comprises providing, by the processor, one of the first coaching message, the second coaching message, and the third coaching message based on a variation in the heart rate and a difference between the heart rate and a preset target heart rate.

3. A non-transitory computer-readable storage medium storing instructions that, when executed by a processor, cause the processor to perform the method of claim 1.

4. The method of claim 1, wherein the providing of the coaching message is performed by a guider.

5. The method of claim 1, wherein the providing of the coaching message is provided using a display, an audio guide, or a vibration.

6. The method of claim 1, wherein the method further comprises executing instructions, stored in a memory, that configure the processor to perform the providing of the coaching message, the adjusting of the exercise intensity, and the providing of the exercise program.

7. A method of providing an adjustable exercise program, the method employing a heart rate sensor worn by a user during performance of the exercise program, and a processor in communication with the sensor and configured to provide a coaching message to the user and adjust the exercise program, the method comprising:
providing, by the processor, a coaching message to the user to coach a training pace in the exercise program based on a heart rate, detected by the heart rate sensor, of a user performing the exercise program;
adjusting, by the processor, an exercise intensity of a current set of exercises of the exercise program based on the coaching message;
providing, by the processor, the exercise program based on the adjusted exercise intensity; and
adjusting, by the processor, an exercise level of the exercise program after a termination of the exercise program based on any one or any combination of any two or more of a heart rate of the user measured during an exercise of the current set, a rating of perceived exertion (RPE) of the user for the exercise of the current set, and a coaching message history of the current set.

8. The method of claim 7, wherein the adjusting the exercise level comprises any one or any combination of any two or more of:
calculating, by the processor, a cumulative heart rate difference rate based on a preset target cumulative heart rate and a first cumulative heart rate, the preset target cumulative heart rate being based on a preset target heart rate of the user during the exercise of the current set of exercises, and the first cumulative heart rate being based on the heart rate of the user measured during the exercise of the current set of exercises;
calculating, by the processor, a message score based on the coaching message history; and
calculating, by the processor, a time score based on a time during which the measured heart rate is higher than a preset target heart rate and a time during which the measured heart rate is lower than the preset target heart rate.

9. The method of claim 8, wherein the calculating of the message score comprises calculating, by the processor, the message score by applying a first weight to a number of times the first coaching message was provided in the coaching message history, a second weight to a number of times the second coaching message was provided in the coaching message history, and a third weight to a number of times the third coaching message was provided in the coaching message history.

10. The method of claim 8, wherein the adjusting the exercise level comprises adjusting, by the processor, the exercise level of the exercise program based on any one or any combination of any two or more of the cumulative heart rate difference rate, the message score, and the time score.

11. The method of claim 8, wherein the adjusting the exercise level comprises changing, by the processor, the exercise program based on the RPE of the user, and any one or any combination of any two or more of the cumulative heart rate difference rate, the message score, and the time score.

12. The method of claim 7, further comprising storing, by the processor, in an exercise history database, exercise history information including any one or any combination of any two or more of a training result of the current set, a heart rate measured during the exercise of the current set, the RPE of the user for the exercise of the current set, and a coaching history based on the coaching message history of the current set.

13. A method of providing an adjustable exercise program, the method employing a heart rate sensor worn by a user during performance of the exercise program, and a processor in communication with the sensor and configured to provide a coaching message to the user and adjust the exercise program, the method comprising:
   providing, by the processor, a coaching message to the user to coach a training pace in the exercise program based on a heart rate, detected by the heart rate sensor, of a user performing the exercise program;
   adjusting, by the processor, an exercise intensity of a current set of exercises of the exercise program based on the coaching message;
   providing, by the processor, the exercise program based on the adjusted exercise intensity and including a plurality of sets of exercises comprising the current set of exercises;
   obtaining, by the processor, a training effect index for each set of exercises based on exercise history information of the exercise program;
   obtaining a cumulative training effect index for each set of exercises; and
   changing the exercise program based on the cumulative training effect index.

14. The method of claim 13, wherein the obtaining of the training effect index comprises:
   obtaining, by the processor, a first training effect index based on a preset target cumulative heart rate and a first cumulative heart rate, the preset target cumulative heart rate being based on a preset target heart rate of the user during an exercise of the current set of exercises, and the first cumulative heart rate being based on a heart rate of the user measured during the exercise of the current set of exercises; and
   obtaining, by the processor, a second training effect index based on an anaerobic energy consumption rate based on the first cumulative heart rate and a second cumulative heart rate, the second cumulative heart rate being based on a steady-state heart rate of the user measured during the exercise.

15. The method of claim 14, wherein the obtaining of the first training effect index comprises:
   calculating, by the processor, a cumulative heart rate difference rate based on the first cumulative heart rate and the preset target cumulative heart rate; and
   obtaining, by the processor, the first training effect index based on a result of comparing the cumulative heart rate difference rate to a preset threshold.

16. The method of claim 14, wherein the obtaining of the second training effect index comprises:
   calculating, by the processor, the anaerobic energy consumption rate based on the first cumulative heart rate and the second cumulative heart rate; and
   obtaining, by the processor, the second training effect index based on a result of comparing the anaerobic energy consumption rate to a preset threshold.

17. The method of claim 13, wherein the changing comprises:
   comparing, by the processor, the cumulative training effect index to a preset threshold; and
   changing, by the processor, the exercise program based on a result of the comparing.

18. An apparatus comprising:
   a heart rate sensor configured to measure a heart rate of a user performing an exercise program; and
   a processor configured to
      provide a coaching message for coaching a training pace in the exercise program based on the measured heart rate,
      adjust an exercise intensity of a current set of exercises of the exercise program based on the coaching message,
      provide the exercise program based on the adjusted exercise intensity, and
      calculate, after a termination of the exercise program, any one or any combination of any two or more of
         a cumulative heart rate difference rate based on a preset target cumulative heart rate and a first cumulative heart rate, the preset target cumulative heart rate being based on a preset target heart rate of the user during an exercise of the current set of exercises, and the first cumulative heart rate being based on a heart rate of the user measured during the exercise of the current set,
         a message score based on a coaching message history, and
         a time score based on a time during which the heart rate measured during the exercise of the current set is higher than a preset target heart rate and a time during which the measured heart rate is lower than the preset target heart rate, wherein
      the processor is further configured to adjust an exercise level of the exercise program based on any one or any combination of any two or more of the cumulative heart rate difference rate, the message score, and the time score.

19. The apparatus of claim 18, wherein the processor is further configured to provide any one or any combination of any two or more of a first coaching message, a second coaching message, and a third coaching message based on a variation in the heart rate and a difference between the heart rate and a preset target heart rate, and adjust the exercise intensity of the current set of exercises in response to a number of times that each of the first coaching message and the third coaching message is consecutively provided being greater than a preset number of times.

20. The apparatus of claim 18, further comprising a memory storing instructions, which when executed by the processor configure the processor to perform the providing of the coaching message, the adjusting of the exercise intensity, the providing of the exercise program, the calculating, and the adjusting of the exercise level of the exercise program.

21. An apparatus comprising:
a heart rate sensor configured to measure a heart rate of a user performing an exercise program; and
a processor configured to provide a coaching message for coaching a training pace in the exercise program based on the measured heart rate, adjust an exercise intensity of a current set of exercises of the exercise program based on the coaching message, and provide the exercise program based on the adjusted exercise intensity,
wherein the exercise program comprises a plurality of sets of exercises comprising the current set of exercises, and
the processor is further configured to obtain a training effect index for each set of exercises based on exercise history information of the exercise program, obtain a cumulative training effect index for each set of exercises, and change the exercise program based on the cumulative training effect index.

* * * * *

UNITED STATES PATENT AND TRADEMARK OFFICE
CERTIFICATE OF CORRECTION

PATENT NO. : 10,360,806 B2
APPLICATION NO. : 15/059879
DATED : July 23, 2019
INVENTOR(S) : Dae-Guen Jang et al.

It is certified that error appears in the above-identified patent and that said Letters Patent is hereby corrected as shown below:

On the Title Page

(73) Assignee should read:
Samsung Electronics Co., Ltd., Suwon-si (KR);
University-Industry Cooperation Group of Kyung Hee University, Yongin-si (KR)

Signed and Sealed this
Twelfth Day of November, 2019

Andrei Iancu
*Director of the United States Patent and Trademark Office*